US00RE49222E

(19) United States
(12) Reissued Patent
Adachi et al.

(10) Patent Number: US RE49,222 E
(45) Date of Reissued Patent: Sep. 27, 2022

(54) FLUORINE-CONTAINING COMPLEX COMPOUND, AND PRODUCTION METHOD FOR FLUORINE-CONTAINING ORGANIC COMPOUND EMPLOYING SAME

(71) Applicants: DAIKIN INDUSTRIES, LTD., Osaka (JP); OSAKA UNIVERSITY, Osaka (JP)

(72) Inventors: Kenji Adachi, Osaka (JP); Takashi Shibanuma, Osaka (JP); Takabumi Nagai, Osaka (JP); Sensuke Ogoshi, Osaka (JP); Masato Ohashi, Osaka (JP)

(73) Assignees: DAIKIN INDUSTRIES, LTD., Osaka (JP); OSAKA UNIVERSITY, Osaka (JP)

(21) Appl. No.: 16/668,703

(22) Filed: Oct. 30, 2019

Related U.S. Patent Documents

Reissue of:
(64) Patent No.: 9,802,963
Issued: Oct. 31, 2017
Appl. No.: 15/026,356
PCT Filed: Oct. 2, 2014
PCT No.: PCT/JP2014/076474
§ 371 (c)(1),
(2) Date: Mar. 31, 2016
PCT Pub. No.: WO2015/050236
PCT Pub. Date: Apr. 9, 2015

(30) Foreign Application Priority Data

Oct. 2, 2013 (JP) ..... JP2013-207624

(51) Int. Cl.

| | |
|---|---|
| ***C07F 1/08*** | (2006.01) |
| ***C07B 37/04*** | (2006.01) |
| ***C07C 17/263*** | (2006.01) |
| ***C07C 25/13*** | (2006.01) |
| ***C07C 37/18*** | (2006.01) |
| ***C07C 39/367*** | (2006.01) |
| ***C07C 41/30*** | (2006.01) |
| ***C07C 43/225*** | (2006.01) |

(Continued)

(52) U.S. Cl.
CPC ..... *C07F 1/08* (2013.01); *C07B 37/04* (2013.01); *C07C 17/263* (2013.01); *C07C 25/13* (2013.01); *C07C 37/18* (2013.01); *C07C 39/367* (2013.01); *C07C 41/30* (2013.01); *C07C 43/225* (2013.01); *C07C 45/45* (2013.01); *C07C 45/61* (2013.01); *C07C 45/68* (2013.01); *C07C 47/55* (2013.01); *C07C 49/233* (2013.01); *C07C 49/235* (2013.01); *C07C 49/84* (2013.01); *C07C 67/00* (2013.01); *C07C 67/30* (2013.01); *C07C 67/343* (2013.01); *C07C 69/65* (2013.01); *C07C 69/76* (2013.01); *C07C 69/78* (2013.01); *C07C 209/68* (2013.01); *C07C 253/30* (2013.01); *C07C 255/50* (2013.01); *C07C 381/00* (2013.01); *C07D 213/26* (2013.01); *C07D 307/87* (2013.01); *C07D 333/12* (2013.01); *C07F 5/02* (2013.01); *C07F 5/04* (2013.01); *C07F 7/081* (2013.01); *C07F 7/083* (2013.01); *C07F 7/12* (2013.01); *C07F 7/18* (2013.01)

(58) Field of Classification Search
CPC .... C07F 1/08; C07F 7/081; C07F 5/04; C07F 7/083; C07F 5/02; C07F 7/12; C07F 7/18; C07C 45/68; C07C 25/13; C07C 45/61; C07C 67/30; C07C 69/78; C07C 255/50; C07C 67/00; C07C 67/343; C07C 37/18; C07C 69/65; C07C 39/367; C07C 69/76; C07C 41/30; C07C 43/225; C07C 209/68; C07C 45/45; C07C 381/00; C07C 47/55; C07C 49/233; C07C 49/235; C07C 253/30; C07C 49/84; C07C 17/263; C07D 333/12; C07D 213/26; C07D 307/87; C07B 37/04
See application file for complete search history.

(56) References Cited

U.S. PATENT DOCUMENTS

| | | | |
|---|---|---|---|
| 3,297,591 | A | 1/1967 | Chow |
| 3,812,177 | A | 5/1974 | Engelhardt et al. |

(Continued)

FOREIGN PATENT DOCUMENTS

| | | |
|---|---|---|
| CA | 995250 | 8/1976 |
| DE | 101 29 335 | 1/2003 |

(Continued)

OTHER PUBLICATIONS

Machine English language translation of EP 1889894 A1 to Bernatz (Year: 2008).*

(Continued)

*Primary Examiner* — Alan D Diamond
(74) *Attorney, Agent, or Firm* — Wenderoth, Lind & Ponack, L.L.P.

(57) ABSTRACT

An object of the present invention is to enable the synthesis of various fluorine-containing compounds having an organic group at both terminals of their tetrafluoroethylene structure (—$CF_2$—$CF_2$—). The present invention provides a fluorine-containing complex compound including a fluorine-containing organic metal compound represented by formula (1a):

$$R^1—CF_2—CF_2-M^1 \quad (1a)$$

wherein $M^1$ is a metal selected from the group consisting of copper, zinc, nickel, iron, cobalt, and tin; and $R^1$ represents an organic group, and at least one ligand selected from the group consisting of pyridine ring-containing compounds and phosphines.

7 Claims, No Drawings

(51) Int. Cl.

| | |
|---|---|
| ***C07C 45/45*** | (2006.01) |
| ***C07C 45/61*** | (2006.01) |
| ***C07C 45/68*** | (2006.01) |
| ***C07C 47/55*** | (2006.01) |
| ***C07C 49/233*** | (2006.01) |
| ***C07C 49/235*** | (2006.01) |
| ***C07C 49/84*** | (2006.01) |
| ***C07C 67/00*** | (2006.01) |
| ***C07C 67/30*** | (2006.01) |
| ***C07C 67/343*** | (2006.01) |
| ***C07C 69/65*** | (2006.01) |
| ***C07C 69/76*** | (2006.01) |
| ***C07C 69/78*** | (2006.01) |
| ***C07C 209/68*** | (2006.01) |
| ***C07C 253/30*** | (2006.01) |
| ***C07C 255/50*** | (2006.01) |
| ***C07C 381/00*** | (2006.01) |
| ***C07D 213/26*** | (2006.01) |
| ***C07D 307/87*** | (2006.01) |
| ***C07D 333/12*** | (2006.01) |
| ***C07F 5/02*** | (2006.01) |
| ***C07F 5/04*** | (2006.01) |
| ***C07F 7/08*** | (2006.01) |
| ***C07F 7/12*** | (2006.01) |
| ***C07F 7/18*** | (2006.01) |

(56) References Cited

U.S. PATENT DOCUMENTS

| | | | |
|---|---|---|---|
| 4,665,217 | A | 5/1987 | Reiners et al. |
| 2003/0009060 | A1 | 1/2003 | Marhold et al. |
| 2005/0012070 | A1 | 1/2005 | Inoue et al. |

FOREIGN PATENT DOCUMENTS

| | | | | |
|---|---|---|---|---|
| EP | 1889894 | A1 * | 2/2008 | ..... C09K 19/42 |
| JP | 47-12775 | | 6/1972 | |
| JP | 49-10669 | | 1/1974 | |
| JP | 50-119841 | | 9/1975 | |
| JP | 61-263947 | | 11/1986 | |
| JP | 4-288344 | | 10/1992 | |
| JP | 5-331084 | | 12/1993 | |
| JP | 2002-212163 | | 7/2002 | |
| JP | 2003-26624 | | 1/2003 | |
| JP | 2004-143280 | | 5/2004 | |
| JP | 2004-189715 | | 7/2004 | |
| JP | 2010-224066 | | 10/2010 | |
| JP | 2014-166970 | | 9/2014 | |
| JP | 2014-166971 | | 9/2014 | |
| JP | 2014-169248 | | 9/2014 | |
| JP | 2014-169262 | | 9/2014 | |
| WO | 2012/024564 | | 2/2012 | |

OTHER PUBLICATIONS

Fields et al.. Metal Carbonyl Chemistry. Part IX. Improved Synthiesis and Some Reactions of Tetracarbonylcyclo-octafluorotetramethyleneiron, Journal of Chemical Society [Section A]: Inorganic, Physical, Theoretical, vol. 11, 1970, pp. 1964-1969.

Hu et al., Cobaloxime-Catalyzed Hydroperfluoroalkylation of Electron-Deficient Alkenes with Perfluoroalkyl Halides: Reaction and Mechamsm, Journal of Organic Chemistry, vol. 57(12), 1992, pp. 3339-3342.

Fukuhara et al., Polyfluorination Using IFs, Journal of Organic Chemistry, vol. 75(21), 2010, pp. 7393-7399.

Yagupolsky et al., The Influence of The Trifluoromethyl Group Substituents on the Reactivity of Aromatic Compounds, Zhumal Obshchei Khimii, vol. 34(11), 1964, pp. 3682-3690 (English Translation).

The Chemical Society of Japan Dai 94 Shunki Nenkai Koen Yokoshu IV, 94th, Mar. 12, 2014, p. 1227 (2 B1-06).

Yang et al., (Trifluoromethy 1)copper: A Useful $CF_2$ Transfer Reagent. A Novel Double Insertion of Difluoromethylene into (Pentafluoropheny 1)copper, Journal of the American Chemistry Society, vol. 114, 1992, pp. 4402-4403.

Yang et al., A novel double insertion of the difluoromethylene unit from trifluoromethylcopper into the carbon-copper bond of perfluoroaryl- and perfluorovinylcopper reagents: preparation, mechanism and applications of new fluorinated copper reagents, Journal of Fluorine Chemistry, vol. 102, 2000, pp. 89-103.

Schröder et al., "Synthese und Reaktivität von (2,6-$^i$Pr$_2$Ph-dad)Ni($C_2F_4$)", Journal of Organometallic Chemistry, vol. 408, 1991, pp. C25-C29, with English abstract.

Kirsch et al., "Reductive dimerization of dithianylium salts and fluorodesulfuration: a new synthetic approach to tetraftuoroethylene substructures", Journal of Fluorine Chemistry, 2004, vol. 125, pp. 1025-1029.

Cannon et al., e-Eros Encyclop. of Reagents for Org. Synthes. (2007), John Wiley.*

Gatenyo et al., J. Fluorine Chem. (2009), vol. 130(3), pp. 332-335.*

King, Med. Chem. Principle and Practice (1994), pp. 206-208.*

Litvinas et al., A General Strategy for the Perfluoroalkylation of Arenes and Arylbromides by Using Arylboronate Esters and [(phen)CuRF], Angewandte Chemie, International Edition, vol. 51(2), 2012, pp. 536-539.

Morimoto et al., A Broadly Applicable Copper Reagent for Trifluoromethylations and Perfluoroalkylations of Aryl Iodides and Bromides, Angewandte Chemie, International Edition, vol. 50(16), 2011, pp. 3793-3798.

Fields et al., Metal Carbonyl Chemistry. Part IX. Improved Synthesis and Some Reactions of Tetracarbonylcyclo-octafluorotetramethyleneiron, Journal of Chemical Society [Section A]: Inorganic, Physical, Theoretical, vol. 11, 1970, pp. 1964-1968.

Brunner et al., Asymmetrische Katalysen, Journal of Organometallic Chemistry, vol. 335(1), 1987, pp. 15-27.

Hughes et al., Fluoroalkylation of cobalt complexes: selective reactions at the metal or the cyclopentadienyl ring, Journal of Organometallic Chemistry, vol. 548(1), 1997, pp. 109-112.

Marchese et al., Perfluoroalkyl Derivatives of Chromium and Colbalt Containing Sulphur Donor Ligands, Journal of Organometallic Chemistry, vol. 121(1), 1976, pp. 63-71.

Treichel et al., Ionic Perfluoroalkyl Complexes of Cobalts, Inorganic Chemistry, vol. 4(8), 1965, pp. 1098-1102.

Fukuhara et al., Polyfluorination Using $IF_5$, Journal of Organic Chemistry, vol. 75(21), 2010, pp. 7393-7399.

R.H. Mobbs, Heptafluorobenzyl Bromide, Journal of Fluorine Chemistry, vol. 1(3), 1972, pp. 361-364.

Yagupolsky et al., The Influence of the Trifluoromethyl Group Substituents on the Reactivity of Aromatic Compounds, Zhurnal Obshchei Khimii, vol. 34(11), 1964, pp. 3682-3690 (English Translation).

Knunyants et al., Phenylperfluoro-α-Olefins and ω-Phenylperfluoroalkanoic Acids, Izvestiya Akademii Nauk SSSR, vol. 1, 1967, pp. 68-71.

Saijo et al., Synthesis of $ArCF_2CF_2Ar'$ by Cu(I)-Meditated 1,2-Arylation of TFE, Abstracts of the Fluorine Conference of Japan, 36th, Oct. 3, 2013, pp. 142-143 (Abstract).

Gatenyo et al., Direct Addition of Fluorine to Arylacetylenes, Journal of Fluorine Chemistry, vol. 130, 2009, pp. 332-335.

Hasek et al., The Chemistry of Sulfur Tetrafluoride. II. The Fluorination of Organic Carbonyl Compounds, Journal of the American Chemical Society, vol. 82, 1960, pp. 543-551.

McEwen et al., Addition of Fluorine to Tolanes, Journal of Fluorine Chemistry, vol. 25, 1984, pp. 169-193.

Gregorcic et al., Fluorination with Xenon Difluoride. 20. Fluorination of Halo-Substituted Alkenes, Journal of Organic Chemistry, vol. 44, No. 8, 1979, pp. 1255-1258.

Yang et al., (Trifluoromethyl)copper: A Useful $CF_2$ Transfer Reagent. A Novel Double Insertion of Difluoromethylene into (Pentafluorophenyl)copper, Journal of the American Chemistry Society, vol. 114, 1992, pp. 4402-4403.

(56) References Cited

OTHER PUBLICATIONS

International Search Report dated Dec. 22, 2014 in corresponding International Application No. PCT/JP2014/076474.
Bennett et al., "Successive insertion of tetrafluoroethylene and CO and of tetrafluoroethylene and acetylenes into aryne-nickel(0) bonds", Journal of Chemical Society, 1997, pp. 3105-3114.
Ohashi et al., "Preparation of Trifluorovinyl Compounds by Lithium Salt-promoted Monoalkylation of Tetrafluoroethene", Chem. Lett., vol. 42, 2013, pp. 933-935.
Clark et al., "Reactions of Organotin Compounds, III. Additions of Dimethyltin Dihydride to Simple Olefins", Canadian Journal of Chemistry. vol. 42, 1964, pp. 1288-1293.

* cited by examiner

FLUORINE-CONTAINING COMPLEX COMPOUND, AND PRODUCTION METHOD FOR FLUORINE-CONTAINING ORGANIC COMPOUND EMPLOYING SAME

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD

The present invention relates to a fluorine-containing complex compound and a method for producing a fluorine-containing organic compound using the fluorine-containing complex compound.

BACKGROUND ART

Fluorine-containing organic compounds have very unique properties distinguished from other compounds and due to, for example, the energy scale of the C—F bond, the low polarization of the C—F bond, and the dipole moment of the C—F bond. Because of their unique properties, fluorine-containing organic compounds have a considerably wide range of applications, for example, in resin, rubber, coating compositions, film, water repellents, oil repellents, liquid crystals, dyes, physiologically active substances, and starting materials of these materials, depending on their structure and characteristics.

Tremendous efforts have thus been made in the development of synthesis methods for a variety of fluorine-containing organic compounds.

Of fluorine-containing organic compounds, compounds having an organic group at both terminals of their tetrafluoroethylene structure (—$CF_2$—$CF_2$—) (this structure may be may be referred to hereinafter as "TFE structure"; and these compounds may be may be referred to hereinafter as a "TFE compound") have unique characteristics, and are thus useful as monomers for fluorine-containing polymers applied to fuel cells or as crystal liquid materials, for example.

Non-patent Literature 1 to 4 disclose methods for synthesizing these TFE compounds by fluorinating various compounds.

Non-patent Literature 5 and 6 disclose methods for synthesizing TEL compounds using a fluorine-containing copper compound, for example.

CITATION LIST

Non-Patent Literature

NPL 1: Julia Gatenyo et al., J. Fluorine Chem., 2009, 130, p. 332.

NPL 2: Hasek, W. R. et al., J. Am. Chem. Soc., 1960, 82, p. 543

NPL 3: W. E. McEwen et al., J. Fluorine Chem, 1984, 25, p. 169

NPL 4: Ana Gregorcic et al., J. Org. Chem., 1979, 44, p. 1255

NPL 5: Zhen-Yu Yang et al., J. Am. Chem. SOC., 1992, 114, p. 4402

NPL 6: Zhen-Yu Yang et al., Journal of Fluorine Chemistry, 2000, 102, p. 89

SUMMARY OF INVENTION

Technical Problem

However, the methods disclosed in Non-patent Literature 1 to 4 are not so simple, and do not provide many varieties of TFE compounds. In particular, none of the literature discloses the synthesis of a fluorine-containing compound having a different organic group at both terminals of the TEE structure.

Moreover, the methods disclosed in Non-patent Literature 5 and 6 do not use tetrafluoroethylene as a starting material, and thus obtaining starting materials involves some difficulty.

The production of various TFE compounds using tetrafluoroethylene as a starting material, which is widely used as a starting material monomer for fluorine-containing resin and mass-produced on an industrial scale, will provide a great industrial advantage.

The present invention is thus intended to provide a production method that can use tetrafluoroethylene as a starting material and that enables the synthesis of a variety of fluorine-containing compounds having organic groups at both terminals of their TFE structure.

Solution to Problem

The present inventors conducted extensive research and developed a novel fluorine-containing complex compound produced by using tetrafluoroethylene as a starting material. The inventors also found that the use of the fluorine-containing complex compound enables the synthesis of various fluorine-containing compounds having an organic group at both terminals of their TFE structure and completed the invention.

The present invention includes the following subject matter.

Item 1.

A fluorine-containing complex compound comprising a fluorine-containing organic metal compound represented by formula (1a):

$$R^1—CF_2—CF_2-M^1 \quad (1a)$$

wherein $M^1$ is a metal selected from the group consisting of copper, zinc, nickel, iron, cobalt, and tin; and $R^1$ represents an organic group, and at least one ligand selected from the group consisting of pyridine ring-containing compounds and phosphines.

Item 2.

A method for producing the fluorine-containing complex compound according to Item 1, the method comprising step A of reacting an organic boron compound that is a boronic acid containing a moiety represented by partial structural formula (2a):

$$R^1—B \quad (2a)$$

wherein $R^1$ is as defined in Item 1, or an ester thereof, or a salt thereof, with a metal compound, the at least one ligand, and tetrafluoroethylene, wherein the metal compound is a hydroxide, halide, alkoxide, aryloxide, thioalkoxide, or thioaryloxide of metal $M^1$.

Item 3.

A method for producing a fluorine-containing compound represented by formula (4):

$$R^2—CF_2—CF_2—R^1 \quad (4)$$

wherein $R^1$ is as defined in Item 1; and $R^2$ represents an organic group, the method comprising step B of reacting the fluorine-containing complex compound according to Item 1 with a halogen compound represented by formula (5):

$$X—R^2 \quad (5)$$

wherein $R^2$ is as defined above; and X represents a halogen atom.

Item 4.

A fluorine-containing compound represented by formula (4-1):

$$(R^{a1S}—)_{ma1}R^{a1L}—CF_2—CF_2—R^{a2L}(—R^{a2S})_{ma2} \quad (4\text{-}1)$$

wherein the moiety represented by formula: $(R^{a1S}—)_{ma1}R^{a1L}$ indicates $R^{a1L}$ substituted with ma1 $R^{a1S}$;

the moiety represented by formula: $R^{a2L}(—R^{a2S})_{ma2}$ indicates $R^{a2L}$ substituted with ma2 $R^{a2S}$;

$R^{a1S}$ and $R^{a2S}$ are the same or different, and each represents independently in each occurrence a polymerizable group;

ma1 and ma2 are the same or different, and each represents an integer of 0 or more, and the sum of ma1 and ma2 is 1 or more; and $R^{a1L}$ and $R^{a2L}$ are the same or different, and each represents an aromatic group optionally having, in addition to ma1 $R^{a1S}$ or ma2 $R^{a2S}$, at least one substituent selected from the group consisting of fluoro group, perfluoro organic group, and pentafluorosulfanyl.

Item 5.

A fluorine-containing compound represented by formula (4-2):

$$(R^{a1S}—)_{ma1}R^{a1L}—CF_2—CF_2—R^{a2L}(—R^{a2S})_{ma2} \quad (4\text{-}2)$$

wherein the moiety represented by $(R^{a1S}—)_{ma1}R^{a1L}—$ indicates $R^{a1L}$ substituted with ma1 $R^{a1S}$;

the moiety represented by $—R^{a2L}(—R^{a2S})_{ma2}$ indicates $R^{a2L}$ substituted with ma2 $R^{a2S}$;

$R^{a1S}$ and $R^{a2S}$ are the same or different, and each represents independently in each occurrence acyl optionally substituted with at least one halogen atom;

ma1 and ma2 are the same or different, and each represents an integer of 0 or more, and the sum of ma1 and ma2 is 1 or more; and $R^{a1L}$ and $R^{a2L}$ are the same or different, and each represents (1) an aromatic group optionally having, in addition to ma1 $R^{a1S}$ or ma2 $R^{a2S}$, at least one substituent selected from the group consisting of fluoro group, perfluoro organic group, and pentafluorosulfanyl, or (2) a bond with the proviso that $R^{a1L}$ and $R^{a2L}$ are not a bond at the same time.

Item 6.

A fluorine-containing compound represented by formula (4-3):

$$(R^{a1S}—)_{ma1}R^{a1L}—CF_2—CF_2—R^{a2L}(—R^{a2S})_{ma2} \quad (4\text{-}3)$$

wherein the moiety represented by $(R^{a1S}—)_{ma1}R^{a1L}$ indicates $R^{a1L}$ substituted with ma1 $R^{a1S}$;

the moiety represented by $R^{a2L}$ $(—R^{a2S})_{ma2}$ indicates $R^{a2L}$ substituted with ma2 $R^{a2S}$;

$R^{a1S}$ represents independently in each occurrence 1,3-dioxo-1,3-dihydroisobenzofuran-5-yl optionally having at least one substituent selected from the group consisting of fluoro group, perfluoro organic group, and pentafluorosulfanyl;

$R^{a2S}$ represents independently in each occurrence (1) 1,3-dioxo-1,3-dihydroisobenzofuran-5-yl optionally having at least one substituent selected from the group consisting of fluoro group, perfluoro organic group, and pentafluorosulfanyl, (2) amino, (3) carboxy, or (4) halogenocarbonyl;

ma1 represents an integer of 1 or more;

ma2 represents an integer of 0 or more; and $R^{a1L}$ and $R^{a2L}$ are the same or different, and each represents (1) an aromatic group optionally having, in addition to ma1 $R^{a1S}$ or ma2 $R^{a2S}$, at least one substituent selected from the group consisting of fluoro group, perfluoro organic group, and pentafluorosulfanyl, or a bond with the proviso that when $R^{a2S}$ is (2) amino, (3) carboxy, or (4) halogenocarbonyl, $R^{a2L}$ is (1) an aromatic group optionally having, in addition to $R^{a2S}$, at least one substituent selected from the group consisting of fluoro group, perfluoro organic group, and pentafluorosulfanyl.

Item 7.

A fluorine-containing compound represented by formula (4-4):

$$(R^{a1S}—)_{ma1}R^{a1L}—CF_2—CF_2—R^{a2L}(—R^{a2S})_{ma2} \quad (4\text{-}4)$$

wherein the moiety represented by $(R^{a1S}—)_{ma1}R^{a1L}$ indicates $R^{a1L}$ substituted with ma1 $R^{a1S}$;

the moiety represented by $R^{a2L}(—R^{a2S})_{ma2}$ indicates $R^{a2L}$ substituted with ma2 $R^{a2S}$;

$R^{a1S}$ and $R^{a2S}$ are the same or different, and each represents independently in each occurrence fluoro group, perfluoro organic group, or pentafluorosulfanyl;

ma1 and ma2 are the same or different, and each represents an integer of 0 or more, and the sum of ma1 and ma2 is 1 or more; and $R^{a1L}$ and $R^{a2L}$ are the same or different, and each represents an aromatic group optionally having, in addition to ma1 $R^{a1S}$ or ma2 $R^{a2S}$, at least one alkoxy group.

Item 8.

A fluorine-containing compound represented by formula (4-5):

$$(R^{a1S}—)_{ma1}R^{a1L}—CF_2—CF_2—R^{a2S} \quad (4\text{-}5)$$

wherein the moiety represented by formula: $(R^{a1S})_{ma1}—R^{a1L}$ indicates $R^{a1L}$ substituted with ma1 $R^{a1S}$;

$R^{a1S}$ represents a polymerizable group;

$R^{a2S}$ represents (1) carboxy or its precursor group, or (2) sulfo, or its precursor group;

ma1 represents an integer of 0 or more; and $R^{a1L}$ represents an aromatic group optionally having, in addition to ma1 $R^{a1S}$, at least one substituent selected from the group consisting of fluoro group, perfluoro organic group, and pentafluorosulfanyl.

Advantageous Effects of Invention

The fluorine-containing complex compound according to the present invention can be synthesized by using tetrafluoroethylene as a starting material and enables the synthesis of various TFE compounds (in particular, TFE compounds having a different organic group at both terminals of their TFE structure).

DESCRIPTION OF EMBODIMENTS

As used herein, unless otherwise indicated, examples of a "halogen atom" include fluorine, chlorine, bromine, and iodine.

As used herein, the term "organic group" refers to a group formed by removing one hydrogen atom from an organic compound.

Examples of organic groups include the following:
alkyl optionally having at least one substituent,
alkenyl optionally having at least one substituent,
alkynyl optionally having at least one substituent,
cycloalkyl optionally having at least one substituent,
cycloalkenyl optionally having at least one substituent,
cycloalkadienyl optionally having at least one substituent,
aryl optionally having at least one substituent,
aralkyl optionally having at least one substituent,
non-aromatic heterocyclic group optionally having at least one substituent,
heteroaryl optionally having at least one substituent,
cyano,
aldehyde,
RCO—,
$RSO_2$—,
ROCO—, and
$ROSO_2$—
wherein R is independently
alkyl optionally having at least one substituent,
alkenyl optionally having at least one substituent,
alkynyl optionally having at least one substituent,
cycloalkyl optionally having at least one substituent,
cycloalkenyl optionally having at least one substituent,
cycloalkadienyl optionally having at least one substituent,
aryl optionally having at least one substituent,
aralkyl optionally having at least one substituent,
non-aromatic heterocyclic group optionally having at least one substituent, or
heteroaryl optionally having at least one substituent.

As used herein, the term "perfluoro organic group" refers to an organic group in which all of the hydrogen atoms attached to carbon atoms are substituted with fluorine atoms. The perfluoro organic group may contain ether oxygen. Examples of perfluoro organic groups include perfluoroalkyl (e.g., trifluoromethyl) and perfluoropolyether.

The perfluoro organic group, for example, has a carbon number of 1 to 8, such as trifluoromethyl.

As used herein, the term "perfluoro organic group" may sometimes be denoted by the symbol "Rf."

As used herein, unless otherwise indicated, the term "acyl" encompasses "acryloyl," "alkanoyl," and "aroyl."

As used herein, unless otherwise indicated, the term "aromatic group" encompasses "aryl," and "heteroaryl."

As used herein, unless otherwise indicated, the term "heterocyclic group" encompasses "non-aromatic heterocyclic group," and "heteroaryl."

As used herein, unless otherwise indicated, examples of "alkyl" include linear or branched alkyl having a carbon number of 1 to 10, such as methyl, ethyl, propyl, isopropyl, butyl, isobutyl, sec-butyl, tert-butyl, pentyl, isopentyl, neopentyl, and hexyl.

As used herein, unless otherwise indicated, examples of "alkenyl" include linear or branched alkenyl having a carbon number of 2 to 10, such as vinyl, 1-propen-1-yl, 2-propen-1-yl, isopropenyl, 2-buten-1-yl, 4-penten-1-yl, and 5-hexen-1-yl.

As used herein, unless otherwise indicated, examples of "alkynyl" include linear or branched alkynyl having a carbon number of 2 to 10, such as ethynyl, 1-propyn-1-yl, 2-propyn-1-yl, 4-pentyn-1-yl, and 5-hexyn-1-yl.

As used herein, unless otherwise indicated, examples of "cycloalkyl" include cycloalkyl having a carbon number 3 to 10, such as cyclopropyl, cyclobutyl, cyclopentyl, cyclohexyl, and cycloheptyl.

As used herein, unless otherwise indicated, examples of "cycloalkenyl" include cycloalkenyl having a carbon number of 3 to 10, such as cyclopropenyl, cyclobutenyl, cyclopentenyl, cyclohexenyl, and cycloheptenyl.

As used herein, unless otherwise indicated, examples of "cycloalkadienyl" include cycloalkadienyl having a carbon number of 4 to 10, such as cyclobutadienyl, cyclopentadienyl, cyclohexadienyl, cycloheptadienyl, cyclooctadienyl, cyclononadienyl, and cyclodecadienyl.

As used herein, unless otherwise indicated, examples of "alkoxy" include linear or branched alkoxy having a carbon number of 1 to 10, such as methoxy, ethoxy, propoxy, isopropoxy, butoxy, isobutoxy, sec-butoxy, pentyloxy, and hexyloxy.

As used herein, unless otherwise indicated, the "alkanoyl" refers to a group represented by formula: R—CO— wherein R represents alkyl.

As used herein, unless otherwise indicated, the "aryl" may be monocyclic, dicyclic, tricyclic, or tetracyclic.

As used herein, unless otherwise indicated, the "aryl" may be aryl having a carbon number of 6 to 18.

As used herein, unless otherwise indicated, examples of "aryl" include phenyl, 1-naphthyl, 2-naphthyl, 2-biphenyl, 3-biphenyl, 4-biphenyl, and 2-anthryl.

As used herein, unless otherwise indicated, examples of "aralkyl" include benzyl, phenethyl, diphenylmethyl, 1-naphthyl methyl, 2-naphthyl methyl, 2,2-diphenylethyl, 3-phenylpropyl, 4-phenylbutyl, 5-phenylpentyl, 2-biphenylylmethyl, 3-biphenylylmethyl, and 4-biphenylylmethyl.

As used herein, unless otherwise indicated, the "aroyl" refers to a group represented by formula: R—CO— wherein R represents aryl.

As used herein, unless otherwise indicated, the "non-aromatic heterocyclic group" may be monocyclic, dicyclic, tricyclic, or tetracyclic.

As used herein, unless otherwise indicated, the "non-aromatic heterocyclic group" may be, for example, a non-aromatic heterocyclic group containing, in addition to carbon, 1 to 4 heteroatoms selected from oxygen, sulfur, and nitrogen as an annular atom.

As used herein, unless otherwise indicated, the "non-aromatic heterocyclic group" may be saturated or unsaturated.

As used herein, unless otherwise indicated, examples of "non-aromatic heterocyclic group" include tetrahydrofuryl, oxazolidinyl, imidazolinyl (e.g., 1-imidazolinyl, 2-imidazolinyl, and 4-imidazolinyl), aziridinyl (e.g., 1-aziridinyl and 2-aziridinyl), azetidinyl (e.g., 1-azetidinyl and 2-azetidinyl), pyrrolidinyl (e.g., 1-pyrrolidinyl, 2-pyrrolidinyl, and 3-pyrrolidinyl), piperidinyl (e.g., 1-piperidinyl, 2-piperidinyl, and 3-piperidinyl), azepanyl (e.g., 1-azepanyl, 2-azepanyl, 3-azepanyl, and 4-azepanyl), azocanyl (e.g., 1-azocanyl, 2-azocanyl, 3-azocanyl, and 4-azocanyl), piperazinyl (e.g., 1,4-piperazin-1-yl, and 1,4-piperazin-2-yl), diazepinyl (e.g., 1,4-diazepin-1-yl, 1,4-diazepin-2-yl, 1,4-diazepin-5-yl, and 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, and 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, and dihydroquinolyl.

As used herein, unless otherwise indicated, the "heteroaryl" may be, for example, a monocyclic-, dicyclic-, tricyclic-, or tetracyclic-, 5 to 18-membered heteroaryl.

As used herein, unless otherwise indicated, the "heteroaryl" may be, for example, heteroaryl containing, in addition to carbon, 1 to 4 heteroatoms selected from oxygen, sulfur, and nitrogen as an annular atom. The heteroaryl may have a carbon number of, for example, 3 to 17.

As used herein, unless otherwise indicated, the "heteroaryl" encompasses "monocyclic heteroaryl" and "aromatic fused heterocyclic group."

As used herein, unless otherwise indicated, examples of "monocyclic heteroaryl" include pyrrolyl (e.g., 1-pyrrolyl, 2-pyrrolyl, and 3-pyrrolyl), furyl (e.g., 2-furyl and 3-furyl), thienyl (e.g., 2-thienyl and 3-thienyl), pyrazolyl (e.g., 1-pyrazolyl, 3-pyrazolyl, and 4-pyrazolyl), imidazolyl (e.g., 1-imidazolyl, 2-imidazolyl, and 4-imidazolyl), isooxazolyl (e.g., 3-isooxazolyl, 4-isooxazolyl, and 5-isooxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl, and 1,2,4-triazol-3-yl), oxadiazolyl (e.g., 1,2,4-oxadiazol-3-yl and 1,2,4-oxadiazol-5-yl), thiadiazolyl (e.g., 1,2,4-thiadiazol-3-yl and 1,2,4-thiadiazol-5-yl), tetrazolyl, pyridyl (e.g., 2-pyridyl, 3-pyridyl, and 4-pyridyl), and pyridazinyl (e.g., 3-pyridazinyl and 4-pyridazinyl), pyrimidinyl (e.g., 2-pyrimidinyl, 4-pyrimidinyl, and 5-pyrimidinyl), and pyrazinyl.

As used herein, unless otherwise indicated, examples of "aromatic fused heterocyclic group" include isoindolyl (e.g., 1-isoindolyl, 2-isoindolyl, 3-isoindolyl, 4-isoindolyl, 5-isoindolyl, 6-isoindolyl, and 7-isoindolyl), indolyl (e.g., 1-indolyl, 2-indolyl, 3-indolyl, 4-indolyl, 5-indolyl, 6-indolyl, and 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, and 7-benzo[b]furanyl), benzo[c]furanyl (e.g., 1-benzo[c]furanyl, 4-benzo[c]furanyl, and 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, and 7-benzo[b]thienyl), benzo[c]thienyl (e.g., 1-benzo[c]thienyl, 4-benzo[c]thienyl, and 5-benzo[c]thienyl), indazolyl (e.g., 1-indazolyl, 2-indazolyl, 3-indazolyl, 4-indazolyl, 5-indazolyl, 6-indazolyl, and 7-indazolyl), benzoimidazolyl (e.g., 1-benzoimidazolyl, 2-benzoimidazolyl, 4-benzoimidazolyl, and 5-benzoimidazolyl), 1,2-benzoisooxazolyl (e.g., 1,2-benzoisoxazol-3-yl, 1,2-benzoisoxazol-4-yl, 1,2-benzoisoxazol-5-yl, 1,2-benzoisoxazol-6-yl, and 1,2-benzoisoxazol-7-yl), benzoxazolyl (e.g., 2-benzoxazolyl, 4-benzoxazolyl, 5-benzoxazolyl, 6-benzoxazolyl, and 7-benzoxazolyl), 1,2-benzoisothiazolyl (e.g., 1,2-benzoisothiazol-3-yl, 1,2-benzoisothiazol-4-yl, 1,2-benzoisothiazol-5-yl, 1,2-benzoisothiazol-6-yl, and 1,2-benzoisothiazol-7-yl), benzothiazolyl (e.g., 2-benzothiazolyl, 4-benzothiazolyl, 5-benzothiazolyl, 6-benzothiazolyl, and 7-benzothiazolyl), isoquinolyl (e.g., 1-isoquinolyl, 3-isoquinolyl, 4-isoquinolyl, and 5-isoquinolyl) quinolyl (e.g., 2-quinolyl, 3-quinolyl, 4-quinolyl, 5-quinolyl, and 8-quinolyl), cinnolinyl (e.g., 3-cinnolinyl, 4-cinnolinyl, 5-cinnolinyl, 6-cinnolinyl, 7-cinnolinyl, and 8-cinnolinyl), phthalazinyl (e.g., 1-phthalazinyl, 4-phthalazinyl, 5-phthalazinyl, 6-phthalazinyl, 7-phthalazinyl, and 8-phthalazinyl), quinazolinyl (e.g., 2-quinazolinyl, 4-quinazolinyl, 5-quinazolinyl, 6-quinazolinyl, 7-quinazolinyl, and 8-quinazolinyl), quinoxalinyl (e.g., 2-quinoxalinyl, 3-quinoxalinyl, 5-quinoxalinyl, 6-quinoxalinyl, 7-quinoxalinyl, and 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, and pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, and imidazo[1,2-a]pyridin-8-yl).

Fluorine-Containing Complex Compound

The fluorine-containing complex compound according to the present invention (which may be may be referred to hereinafter as "fluorine-containing complex compound (1)") comprises a fluorine-containing organic metal compound represented by formula (1a):

$$R^1—CF_2—CF_2-M^1 \quad (1a)$$

wherein $M^1$ is a metal selected from the group consisting of copper, zinc, nickel, iron, cobalt, and tin; and $R^1$ represents an organic group (which may be may be referred to hereinafter as "fluorine-containing organic metal compound (1a)"), and at least one ligand selected from the group consisting of pyridine ring-containing compounds and phosphines (which may be may be referred to hereinafter as "ligand (1b)").

Fluorine-containing complex compound (1) preferably consists of fluorine-containing organic metal compound (1a) and at least one ligand (1b).

The metal represented by $M^1$ forms a coordinate bond with at least one ligand (1b).

$M^1$ is preferably copper (preferably, copper(I)).

$R^1$ is preferably alkyl optionally having at least one substituent,
alkenyl optionally having at least one substituent,
alkynyl optionally having at least one substituent,
cycloalkyl optionally having at least one substituent,
cycloalkenyl optionally having at least one substituent,
cycloalkadienyl optionally having at least one substituent,
aralkyl optionally having at least one substituent,
aryl optionally having at least one substituent (more preferably $C_{6-18}$aryl optionally having at least one substituent), or heteroaryl optionally having at least one substituent (more preferably, 5 to 18-membered heteroaryl optionally having at least one substituent).

In the alkyl optionally having at least one substituent,
alkenyl optionally having at least one substituent,
alkynyl optionally having at least one substituent,
cycloalkyl optionally having at least one substituent,
cycloalkenyl optionally having at least one substituent,
cycloalkadienyl optionally having at least one substituent,
aralkyl optionally having at least one substituent,
aryl optionally having at least one substituent, and
heteroaryl optionally having at least one substituent,
preferable examples of a "substituent" include halogen (preferably fluorine), cyano, amino, alkoxy, perfluoro organic group (preferably $C_{1-8}$perfluoro organic group, more preferably trifluoromethyl), pentafluorosulfanyl ($F_5S$—), and polymerizable group.

In addition to these, examples of the substituent for the "aryl optionally having at least one substituent" include divalent groups, such as carbonyloxycarbonyl (—CO—O—

CO—). The divalent group forms a fused ring (e.g., 1,3-dioxo-1,3-dihydroisobenzofuran) with one benzene ring in aryl.

As used herein, examples of a "polymerizable group" include:

(1) cyano,
(2) aldehyde,
(3) alkenyl optionally substituted with at least one halogen atom (e.g., vinyl optionally substituted with at least one halogen atom),
(4) alkynyl optionally substituted with at least one substituent selected from the group consisting of halogen and trimethylsilyl (e.g., optionally trimethylsilylated ethynyl),
(5) epoxy,
(6) (meta)acryloyl optionally substituted with at least one halogen atom (e.g., methacryloyl, acryloyl, 2-fluoroacryloyl, and 2-chloroacryloyl), and
(7) alkyl and alkoxy each substituted with at least one substituent selected from the group consisting of:
(a) cyano group,
(b) aldehyde,
(c) alkynyl optionally substituted with at least one halogen atom,
(d) alkenyl optionally substituted with at least one halogen atom (e.g., vinyl optionally substituted with at least one halogen atom),
(e) epoxy, and
(f) (meta)acryloyl optionally substituted with at least one halogen atom (e.g., methacryloyl, acryloyl, 2-fluoroacryloyl, and 2-chloroacryloyl).

$R^1$ is more preferably,
alkenyl optionally having at least one substituent,
alkynyl optionally having at least one substituent,
aryl optionally having at least one substituent, or heteroaryl optionally having at least one substituent.

Examples of the "pyridine ring-containing compounds," stated as ligand (1b), include phenanthroline (e.g., 1,10-phenanthroline), 2,2'-bipyridyl, pyridine, methyl pyridine, and lutidine (e.g., 2,6-lutidine).

The "phosphine," stated as ligand (1b), are preferably trialkylphosphine and triarylphosphine. Specific examples of trialkylphosphines include tri($C_{3-20}$alkyl)phosphines, such as tricyclohexylphosphine, triisopropylphosphine, tri-t-butylphosphine, trihexylphosphine, triadamantylphosphine, tricyclopentylphosphine, di-t-butylmethylphosphine, tribicyclo[2,2,2]octylphosphine, and trinorbornylphosphine.

Specific examples of triarylphosphines include tri(monocyclic aryl)phosphines, such as triphenylphosphine, trimesitylphosphine, and tri(o-tolyl)phosphine. Of these, triphenylphosphine, tricyclohexylphosphine, and tri-t-butylphosphine are preferable.

Ligand (1b) is preferably a bidentate ligand.

Preferable example include 1,10-phenanthroline.

The coordination number of ligand (1b) bound to fluorine-containing organic metal compound (1a) varies depending on the oxidation number of metal $M^1$ and the number of coordinating atoms of ligand (1b), but is preferably 1 to 3.

Method for Producing Fluorine-Containing Complex Compound

The fluorine-containing complex compound according to the present invention can be produced by, for example, the production method described below.

A method for producing the fluorine-containing complex compound according to the present invention comprises step A of reacting an organic boron compound that is a boronic acid containing a moiety represented by partial structural formula (2a):

$R^1$—B (2a) wherein $R^1$ is as defined above, or an ester thereof, or a salt thereof (which may be may be referred to hereinafter as "organic boron compound (2)") with a metal compound that is a hydroxide, halide, alkoxide, aryloxide, thioalkoxide, or thioaryloxide of metal $M^1$ (which may be may be referred to hereinafter as "metal compound (3)"),
ligand (1b), and
tetrafluoroethylene.

Examples of organic boron compound (2) include boronic acid represented by formula (2-1), esters thereof, and salts thereof:

$R^1$—$BY_2$ (2-1)

wherein $R^1$ is as defined above;

Y represents independently hydroxy or alkoxy; and two alkoxy groups represented by Y may be crosslinked to each other.

Examples of alkoxy represented by Y include $C_{1-6}$alkoxy.

When both Ys are hydroxy, organic boron compound (2) is a boronic acid.

When two alkoxy groups represented by $Y_2$ are crosslinked to each other, organic boron compound (2) is a boronic acid ester.

In this case, the moiety represented by $BY_2$ in formula (2-1) indicates, for example, the following.

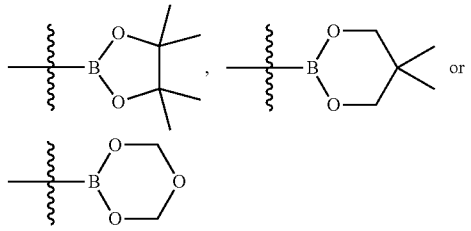

Organic boron compound (2) can be produced by a known method or a method according to the known method, and is also commercially available.

Examples of halides of metal compound (3) include fluorides, chlorides, bromides, and iodides of metal compound (3).

The alkoxy moiety of alkoxide in metal compound (3) is preferably a group represented by formula: RO— wherein R is linear or branched alkyl having a carbon number of 1 to 10, more preferably quaternary alkoxy, and further more preferably tert-butoxy.

The aryloxy moiety of phenoxide in metal compound (3) is preferably a group represented by formula: RO— wherein R is optionally substituted aryl having a carbon number of 6 to 10, and more preferably phenoxy.

The alkylthio moiety of thioalkoxide in metal compound (3) is preferably a group represented by formula: RS— wherein R is linear or branched alkyl having a carbon number of 1 to 10.

The arylthio moiety of thiophenoxide in metal compound (3) is preferably a group represented by formula: RO— wherein R is optionally substituted aryl having a carbon number of 6 to 10, and more preferably phenylsulfanyl.

Metal compound (3) is preferably alkoxide in which the alkoxy moiety is quaternary alkoxy, and more preferably tert-butoxide.

Metal compound (3) can be produced by a known method or a method according to the known method, and is also commercially available.

Ligand (1b) described for the fluorine-containing complex compound mentioned above is used as ligand (1b). As used herein, ligand (1b) in the fluorine-containing complex compound and a starting material compound corresponding to this ligand (1b) are both referred to as "ligand (1b)". Both ligands (1b) are distinguished depending on the context.

Ligand (1b) can be produced by a known method or a method according to the known method, and is also commercially available.

The reaction in step A can be performed by mixing organic boron compound (2), metal compound (3), ligand (1b ), and tetrafluoroethylene (which may be hereinafter abbreviated as "TFE").

The mixing can be performed, for example, by introducing TFE gas into a solution or a suspension of organic boron compound (2), metal compound (3), and ligand (1b).

Examples of solvents for the solution or suspension include diethylether, 1,4-dioxane, acetonitrile, ethyl acetate, ethyl formate, toluene, dimethyl sulfoxide, dimethylformamide, hexane, tetrahydrofuran, and mixtures thereof.

The amount of the solvent is typically within the range of 0.5 to 500 parts by weight, preferably 1 to 100 parts by weight, and more preferably 2.5 to 50 parts by weight per part by weight of organic boron compound (2).

The amount of metal compound (3) is typically within the range of 0.2 to 10 moles, preferably 0.5 to 5 moles, and more preferably 0.8 to 2 moles per mole of organic boron compound (2).

The amount of ligand (1b) is typically within the range of 0.2 to 10 moles, preferably 0.5 to 5 moles, and more preferably 0.8 to 2 moles per mole of organic boron compound (2).

The amount of TFE is typically within the range of 0.5 moles to an excessive amount, preferably 0.8 to 50 moles, and more preferably 1 to 10 moles per mole of organic boron compound (2).

Step A is performed at a temperature within the range of typically −20 to 200° C., preferably 0 to 150° C., and more preferably 20 to 100° C.

The reaction time of step A is within the range of typically 1 minute to 10 days, preferably 5 minutes to 3 days, and more preferably 10 minutes to 1 day.

The obtained fluorine-containing complex compound (1) of the present invention may be used, as it is, for the fluorine-containing compound described below, or may further be purified by a known purification method, such as solvent extraction, desiccation, filtration, distillation, concentration, recrystallization, sublimation, column chromatography, and combinations thereof.

Method for Producing Fluorine-Containing Compound

The method for producing a fluorine-containing compound according to the present invention produces by using the fluorine-containing complex compound of the present invention described above, a fluorine-containing compound represented by formula (4) (which may be may be referred to hereinafter as "fluorine-containing compound (4)"):

$$R^2—CF_2—CF_2—R^1 \quad (4)$$

wherein $R^1$ is as defined above; and $R^2$ represents an organic group.

The production method comprises step B of reacting fluorine-containing complex compound (1) of the present invention with a halogen compound represented by formula (5) (which may be may be referred to hereinafter as "halogen compound (5)"):

$$X—R^2 \quad (5)$$

wherein $R^2$ is as defined above; and

X represents a halogen atom.

$R^1$ is as defined for the "fluorine-containing complex compound."

X is preferably iodine.

$R^2$ is preferably alkenyl optionally having at least one substituent, alkynyl optionally having at least one substituent, aryl optionally having at least one substituent (more preferably $C_{6-18}$aryl optionally having at least one substituent), aralkyl optionally having at least one substituent, heteroaryl optionally having at least one substituent (more preferably 5 to 18-membered heteroaryl optionally having at least one substituent),

RCO—, $RSO_2$—,

ROCO—, or $ROSO_2$— wherein R is independently hydrogen, halogen, aryl, aralkyl, or alkyl.

In the alkenyl optionally having at least one substituent, alkynyl optionally having at least one substituent, aryl optionally having at least one substituent, aralkyl optionally having at least one substituent, and heteroaryl optionally having at least one substituent, examples of a "substituent" include fluoro group, perfluoro organic group (preferably $C_{2-8}$perfluoro organic group, and more preferably trifluoromethyl), pentafluorosulfanyl, and polymerizable group.

$R^2$ may be the same as or different from $R^1$.

The reaction of step B can be performed by mixing fluorine-containing complex compound (1) of the present invention with halogen compound (5).

The mixing can be performed, for example, by adding halogen compound (5) to a suspension of fluorine-containing complex compound (1) in a solvent.

Examples of solvents for the suspension include diethylether, 1,4-dioxane, acetonitrile, ethyl acetate, ethyl formate, toluene, dimethyl sulfoxide, dimethylformamide, hexane, tetrahydrofuran, and mixtures thereof.

The amount of the solvent is typically within the range of 0.5 to 500 parts by weight, preferably 1 to 100 parts by weight, and more preferably 2.5 to 50 parts by weight per part by weight of fluorine-containing complex compound (1).

The amount of halogen compound (5) is typically within the range of 0.2 to 10 moles, preferably 0.5 to 5 moles, and more preferably 0.8 to 2 moles per mole of fluorine-containing complex compound (1).

Step B is performed at a temperature typically within the range of −20 to 200° C., preferably 0 to 150° C., and more preferably 20 to 100° C.

The reaction time of step B is typically within the range of 1 minute to 10 days, preferably 5 minutes to 3 days, and more preferably 10 minutes to 1 day.

Step B may be performed in one pod with step A.

The reactions of step A and step B can be performed in one pod by, for example, mixing organic boron compound (2), metal compound (3), ligand (1b), halogen compound (5), and TFE.

A known technique, such as acylation and alkylation, may be applied to fluorine-containing compound (4) obtained by the production method described above or its intermediate to introduce or replace one or more substituents, thereby producing fluorine-containing compound (4).

Fluorine-containing compound (4) obtained by the production method of the present invention can be used as, for example, monomers for fluorine-containing polymers used in fuel cell materials, and liquid crystal materials.

Fluorine-containing compound (4) obtained by the production method may be used, as it is, as monomers for fluorine-containing polymers used in heat-resistant polymers, fuel cell materials, and the like, and liquid crystal materials. If desired, fluorine-containing compound (4) may be further purified by a known purification method, such as solvent extraction, desiccation, filtration, distillation, concentration, recrystallization, sublimation, column chromatography, and combinations thereof.

Fluorine-Containing Compound (4)

Fluorine-containing compound (4) encompasses novel compounds represented by the following formulae (4-1), (4-2), (4-3), (4-4), and (4-5).

Fluorine-containing compound represented by formula (4-1) (which may be may be referred to hereinafter as "fluorine-containing compound (4-1)"):

$$(R^{a1S}—)_{ma1}R^{a1L}—CF_2—CF_2—R^{a2L}(—R^{a2S})_{ma2} \quad (4\text{-}1)$$

wherein the moiety represented by formula: $(R^{a1S}—)_{ma1}R^{a1L}$ indicates $R^{a1L}$ substituted with ma1 $R^{a1S}$;

the moiety represented by formula: $R^{a2L}$ $(—R^{a2S})_{ma2}$ indicates $R^{a2L}$ substituted with ma2 $R^{a2S}$;

$R^{a1S}$ and $R^{a2S}$ are the same or different, and each represents independently in each occurrence a polymerizable group;

ma1 and ma2 are the same or different, and each represents an integer of 0 or more, and the sum of ma1 and ma2 is 1 or more; and $R^{a1L}$ and $R^{a2L}$ are the same or different, and each represents an aromatic group optionally having, in addition to ma1 $R^{a1S}$ or ma2 $R^{a2S}$, at least one substituent selected from the group consisting of fluoro group, perfluoro organic group (preferably $C_{1-8}$perfluoro organic group, and more preferably trifluoromethyl), and pentafluorosulfanyl.

$R^{a1L}$ and $R^{a2L}$ are preferably the same or different, and are phenyl optionally having, in addition to ma1 $R^{a1S}$ or ma2 $R^{a2S}$, at least one substituent selected from the group consisting of fluoro group, perfluoro organic group (preferably $C_{1-8}$perfluoro organic group, and more preferably trifluoromethyl), and pentafluorosulfanyl.

Of fluorine-containing compound (4-1), the following compounds are preferable.

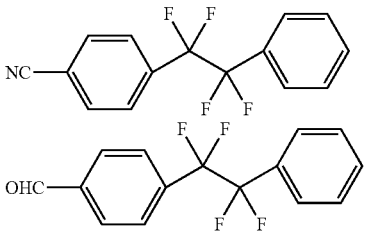

-continued

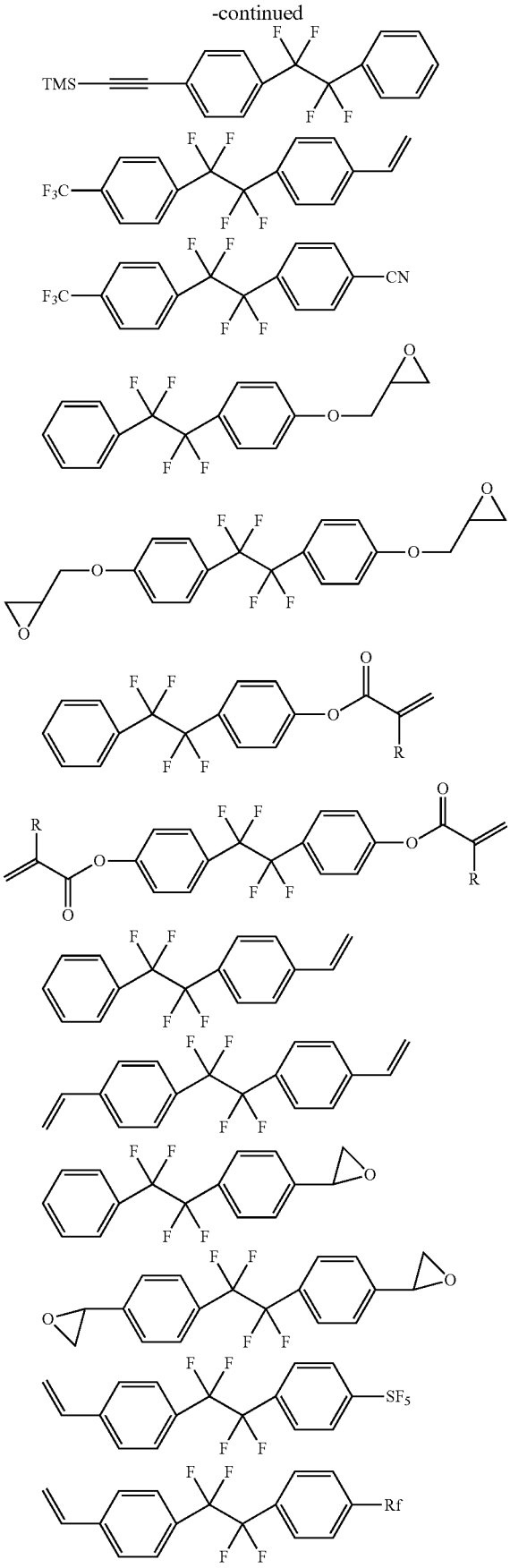

-continued

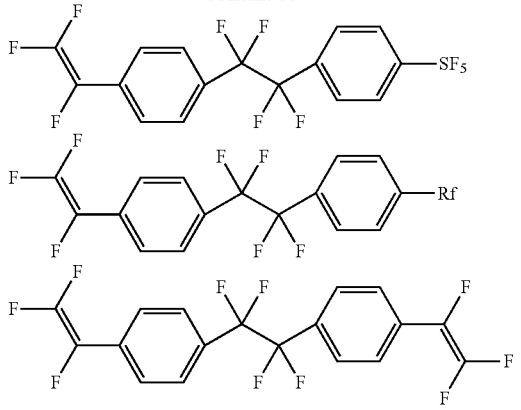

In these formulae, TMS represents trimethylsilyl, and R represents independently hydrogen, methyl, chlorine, or fluorine.

These compounds can be produced by conducting step A and step B described above, and can also be produced by the following method.

(1) The compound represented by formula (4-1-a-3) in the following scheme can be produced by conducting step A and step B described above to thereby produce the compound represented by formula (4-1-a-1) in the scheme and reacting the compound represented by formula (4-1-a-1) with the compound represented by formula (4-1-a-2) as described in the scheme.

Although the compounds represented by formula (4-1-a-1) and formula (4-1-b-1) can be produced by conducting step A and step B, the compounds can also be produced by preparing an intermediate in accordance with step A and step B using a starting material having its hydroxy protected by a known protective group and then deprotecting the protective group by a known method. Examples of known protective groups include trialkylsilyl, alkyl, alkoxyalkyl, benzyl, and acyl.

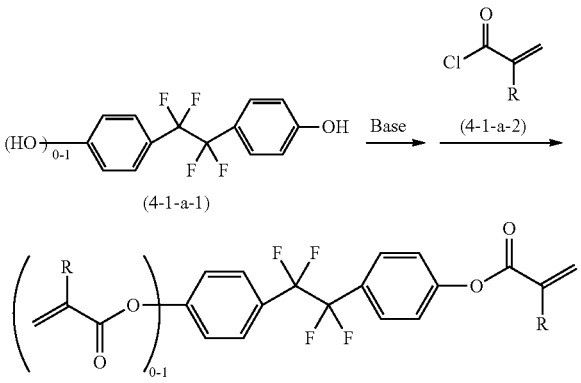

(4-1-a-1)

(4-1-a-3)

R = H, Me, Cl, F

In the scheme, Me represents methyl.

(2) The compound represented by formula (4-1-b-3) in the following scheme can be produced by conducting step A and step B described above to thereby produce the compound represented by formula (4-1-b-1) in the scheme and reacting the compound represented by formula (4-1-b-1) with the compound represented by formula (4-1-b-2) as described in the scheme.

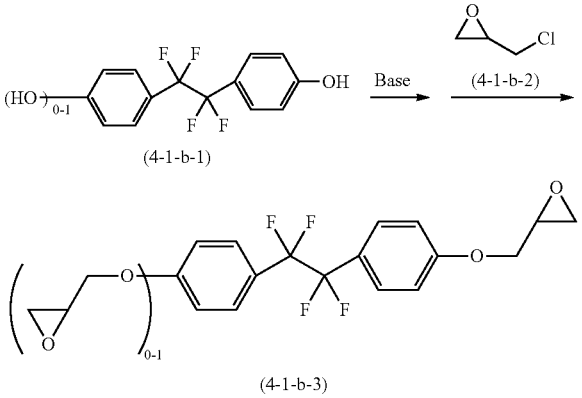

(4-1-b-1)

(4-1-b-3)

(3) The compound represented by formula (4-1-c-2) in the following scheme can be produced by conducting step A and step B to thereby produce the compound represented by formula (4-1-c-1) in the scheme and epoxidizing the compound represented by formula (4-1-c-1) using a hydrogen peroxide solution or meta-chloroperbenzoic acid (MCPBA).

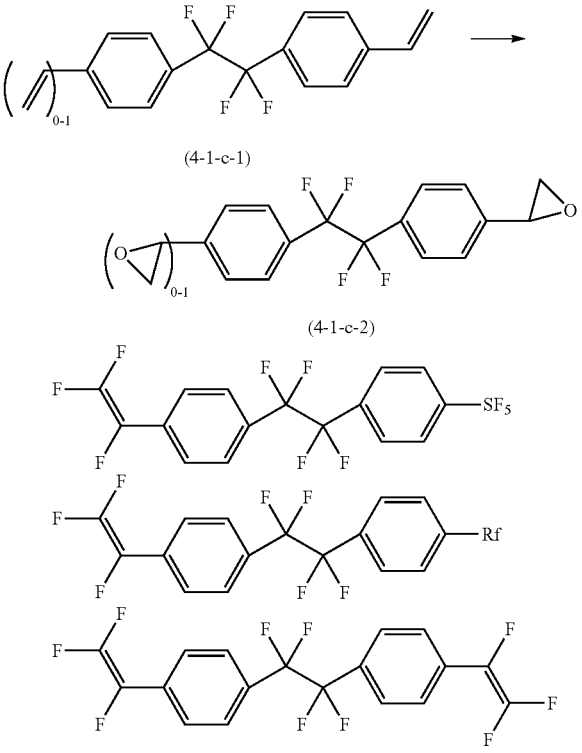

(4-1-c-1)

(4-1-c-2)

These compounds can be produced by conducting step A using an organic boron compound containing trifluorovinyl produced by the method disclosed in WO2012/121345. Thereafter, step B may be performed using a halide containing a predetermined functional group.

Fluorine-containing compound represented by formula (4-2) (which may be may be referred to hereinafter as "fluorine-containing compound (4-2)"):

$$(R^{a1S}—)_{ma1}R^{a1L}—CF_2—CF_2—R^{a2L}(—R^{a2S})_{ma2} \quad (4\text{-}2)$$

wherein the moiety represented by $(R^{a1S}—)_{ma1}R^{a1L}—$ indicates $R^{a1L}$ substituted with ma1 $R^{a1S}$;

the moiety represented by $—R^{a2L}(—R^{a2S})_{ma2}$ indicates $R^{a2L}$ substituted with ma2 $R^{a2S}$;

$R^{a1S}$ and $R^{a2S}$ are the same or different, and each represents independently in each occurrence acyl optionally substituted with at least one halogen atom;

ma1 and ma2 are the same or different, and each represents an integer of 0 or more, and the sum of ma1 and ma2 is 1 or more; and $R^{a1L}$ and $R^{a2L}$ are the same or different, and each represents (1) an aromatic group optionally having, in addition to ma1 $R^{a1S}$ or ma2 $R^{a2S}$, at least one substituent selected from the group consisting of fluoro group, perfluoro organic group (preferably $C_{1-8}$perfluoro organic group, and more preferably trifluoromethyl), and pentafluorosulfanyl, or (2) a bond with the proviso that $R^{a1L}$ and $R^{a2L}$ are not a bond at the same time.

As will be easily understood by a person skilled in the art, when $R^{a1L}$ or $R^{a2L}$ is a bond, ma1 or ma2 is 1, and $R^{a1L}$ or $R^{a2L}$ directly bonds to $—CF_2—CF_2—$.

The same applies to compounds represented by the other formulae.

$R^{a1L}$ and $R^{a2L}$ are preferably the same or different, and each represents (1) phenyl optionally having, in addition to ma1 $R^{a1S}$ or ma2 $R^{a2S}$, at least one substituent selected from the group consisting of fluoro group, perfluoro organic group (preferably $C_{1-8}$perfluoro organic group, and more preferably trifluoromethyl), and pentafluorosulfanyl, or (2) a bond.

Of fluorine-containing compound (4-2), the following compounds are preferable.

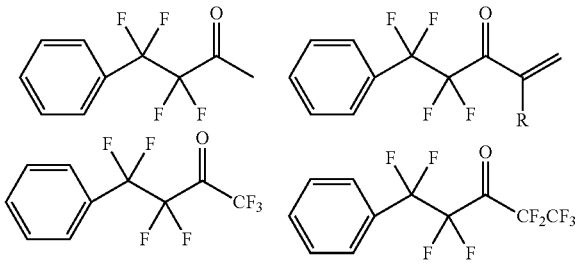

In these formulae, R represents hydrogen, methyl, chlorine, or fluorine.

A fluorine-containing compound represented by formula (4-3) (which may be may be referred to hereinafter as "fluorine-containing compound (4-3)"):

$$(R^{a1S}—)_{ma1}R^{a1L}—CF_2—CF_2—R^{a2L}(—R^{a2S})_{ma2} \quad (4\text{-}3)$$

wherein the moiety represented by $(R^{a1S}—)_{ma1}R^{a1L}$ indicates $R^{a1L}$ substituted with ma1 $R^{a1S}$;

the moiety represented by $R^{a2L}(—R^{a2S})_{ma2}$ indicates $R^{a2L}$ substituted with ma2 $R^{a2S}$;

$R^{a1S}$ represents independently in each occurrence 1,3-dioxo-1,3-dihydroisobenzofuran-5-yl optionally having at least one substituent selected from the group consisting of fluoro group, perfluoro organic group (preferably $C_{1-8}$perfluoro organic group, and more preferably trifluoromethyl), and pentafluorosulfanyl;

$R^{a2S}$ represents independently in each occurrence (1) 1,3-dioxo-1,3-dihydroisobenzofuran-5-yl optionally having at least one substituent selected from the group consisting of fluoro group, perfluoro organic group (preferably $C_{1-8}$perfluoro organic group, and more preferably trifluoromethyl), and pentafluorosulfanyl, (2) amino, (3) carboxy, or (4) halogenocarbonyl;

ma1 represents an integer of 1 or more;

ma2 represents an integer of 0 or more (preferably an integer of 1 or more); and $R^{a1L}$ and $R^{a2L}$ are the same or different, and each represents (1) an aromatic group optionally having, in addition to ma1 $R^{a1S}$ or ma2 $R^{a2S}$, at least one substituent selected from the group consisting of fluoro group, perfluoro organic group (preferably $C_{1-8}$perfluoro organic group, and more preferably trifluoromethyl), and pentafluorosulfanyl, or (2) a bond with the proviso that when $R^{a2S}$ is (2) amino, (3) carboxy, or (4) halogenocarbonyl, $R^{a2L}$ is (1) an aromatic group optionally having, in addition to $R^{a2S}$, at least one substituent selected from the group consisting of fluoro group, perfluoro organic group (preferably $C_{1-8}$perfluoro organic group, and more preferably trifluoromethyl), and pentafluorosulfanyl.

1,3-dioxo-1,3-dihydroisobenzofuran-5-yl is represented by formula:

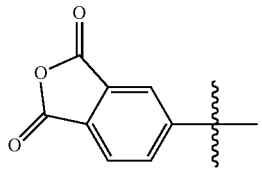

$R^{a1L}$ and $R^{a2L}$ are preferably the same or different, and each represents (1) phenyl optionally having, in addition to ma1 $R^{a1S}$ or ma2 $R^{a2S}$, at least one substituent selected from the group consisting of fluoro group, perfluoro organic group (preferably $C_{1-8}$perfluoro organic group, and more preferably trifluoromethyl), and pentafluorosulfanyl, or (2) a bond.

Of fluorine-containing compound (4-3), the following compounds are preferable.

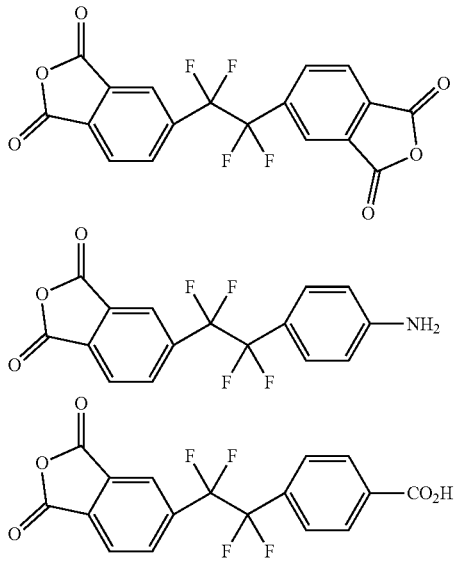

-continued

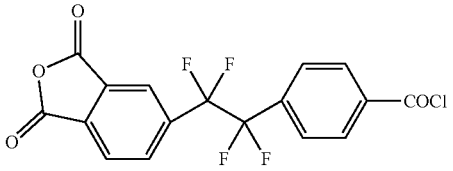

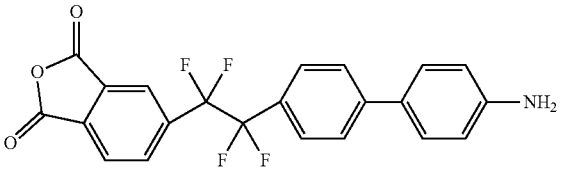

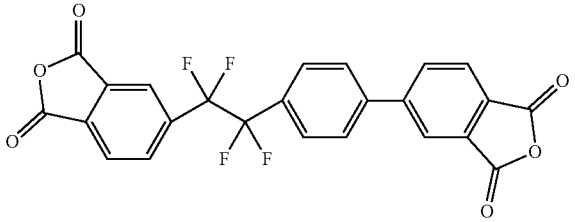

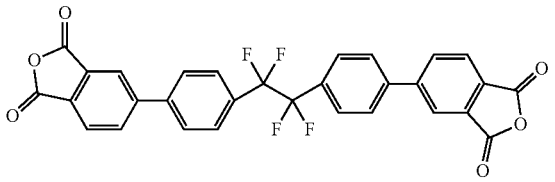

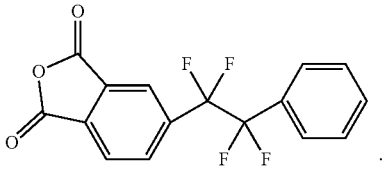

A fluorine-containing compound represented by formula (4-4) (which may be may be referred to hereinafter as "fluorine-containing compound (4-4)"):

$$(R^{a1S}—)_{ma1}R^{a1L}—CF_2—CF_2—R^{a2L}(—R^{a2S})_{ma2} \quad (4\text{-}4)$$

wherein the moiety represented by $(R^{a1S}—)_{ma1}R^{a1L}$ indicates $R^{a1L}$ substituted with ma1 $R^{a1S}$;

the moiety represented by $R^{a2L}(—R^{a2S})_{ma2}$ indicates $R^{a2L}$ substituted with ma2 $R^{a2S}$;

$R^{a1S}$ and $R^{a2S}$ are the same or different, and each represents independently in each occurrence fluoro group, perfluoro organic group (preferably $C_{1-8}$perfluoro organic group, and more preferably trifluoromethyl), or pentafluorosulfanyl;

ma1 and ma2 are the same or different, and each represents an integer of 0 or more, and the sum of ma1 and ma2 is 1 or more; and $R^{a1L}$ and $R^{a2L}$ are the same or different, and each represents an aromatic group optionally having, in addition to ma1 $R^{a1S}$ or ma2 $R^{a2S}$, at least one alkoxy group.

$R^{a1L}$ and $R^{a2L}$ are the same or different, and each represents phenyl or naphthyl optionally having, in addition to ma1 $R^{a1S}$ or ma2 $R^{a2S}$, at least one alkoxy group.

Of fluorine-containing compound (4-4), the following compounds are preferable.

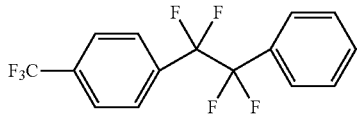

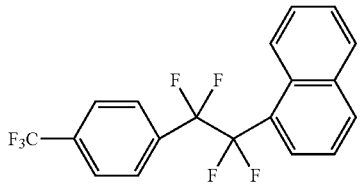

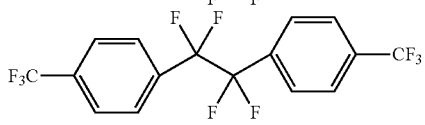

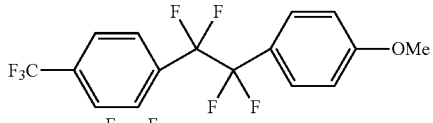

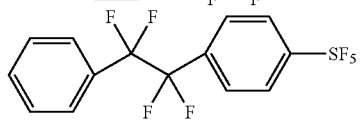

A fluorine-containing compound represented by formula (4-5) (which may be may be referred to hereinafter as "fluorine-containing compound (4-5)"):

$$(R^{a1S}—)_{ma1}R^{a1L}—CF_2—CF_2—R^{a2S} \quad (4\text{-}5)$$

wherein the moiety represented by formula: $(R^{a1S})_{ma1}—R^{a1L}$ indicates $R^{a1L}$ substituted with ma1 $R^{a1S}$;

$R^{a1S}$ represents a polymerizable group;

$R^{a2S}$ represents (1)carboxy or its precursor group, or (2) sulfo or its precursor group;

ma1 represents an integer of 0 or more (preferably an integer of 1 or more); and $R^{a1L}$ represents an aromatic group optionally having, in addition to ma1 $R^{a1S}$, at least one substituent selected from the group consisting of fluoro group, perfluoro organic group (preferably $C_{1-8}$perfluoro organic group, and more preferably trifluoromethyl), and pentafluorosulfanyl.

$R^{a1L}$ is preferably phenyl optionally having, in addition to ma1 $R^{a1S}$, at least one substituent selected from the group consisting of fluoro group, perfluoro organic group (preferably $C_{1-8}$perfluoro organic group, and more preferably trifluoromethyl), and pentafluorosulfanyl.

Of fluorine-containing compound (4-5), the following compounds are preferable.

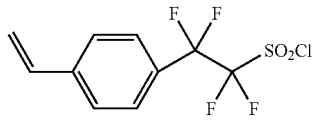

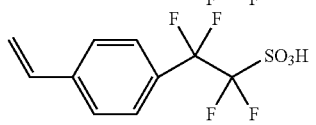

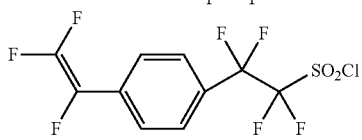

-continued

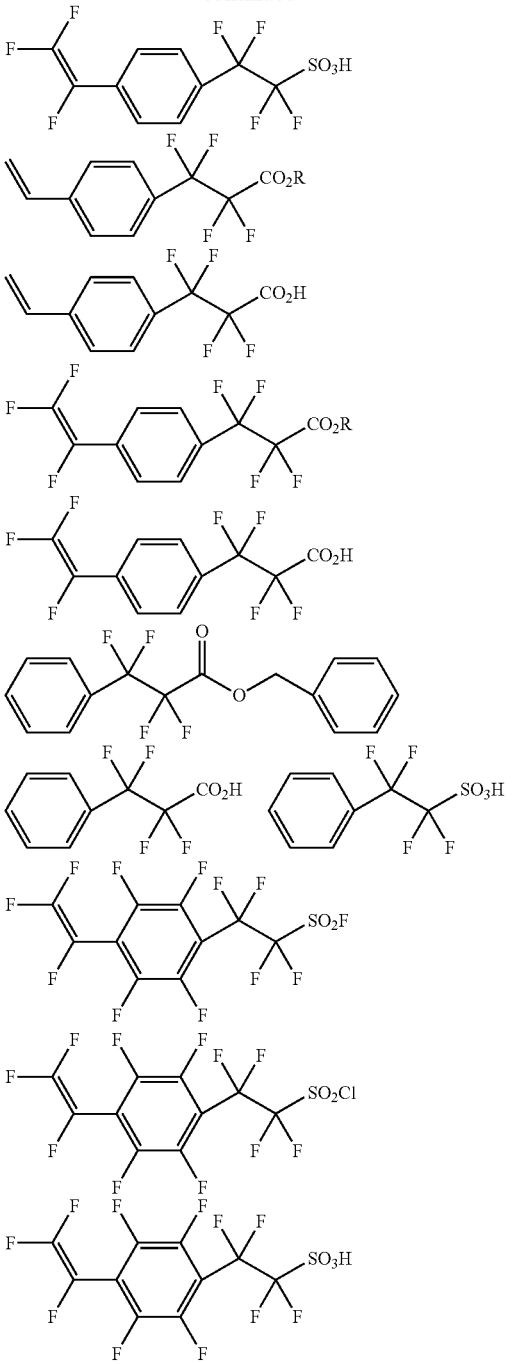

Polyimide

A polyimide can be produced by reacting a diamine with fluorine-containing compound (4-3) in which one $R^{a1S}$ and one $R^{a2S}$ are 1,3-dioxo-1,3-dihydroisobenzofuran-5-yl optionally having at least one substituent selected from the group consisting of fluoro group, perfluoro organic group (preferably $C_{1-8}$perfluoro organic group, and more preferably trifluoromethyl), and pentafluorosulfanyl (which may be may be referred to hereinafter as "fluorine-containing compound (4-3a)").

The polyimide is a novel compound.

The polyimide contains structural unit A represented by the following formula:

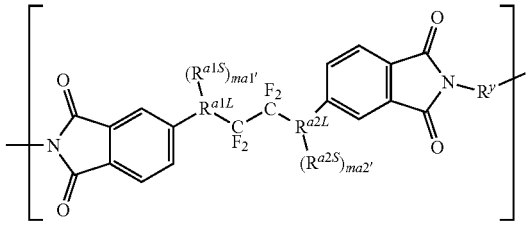

wherein ma1' is (ma1)-1 and represents an integer of 0 or more, ma2' is (ma2)-1 and represents an integer of 0 or more, $R^{a1L}$ and $R^{a2L}$ are the same or different, and each represents an aromatic group or a single bond, $R^y$ represents a divalent organic group, and the other symbols are as defined in formula (4-3).

The aromatic groups represented by $R^{a1L}$ and $R^{a2L}$ are the same as the aromatic groups represented by $R^{a1L}$ and $R^{a2L}$ in formula (4-3).

$R^{a1L}$ and $R^{a2L}$ are both preferably a single bond.

$R^y$ is a group formed by removing two amino groups from the diamine. The diamine as used herein is represented by $H_2N—R^y—NH_2$ wherein $R^y$ represents a divalent organic group.

$R^y$ is preferably arylene optionally having at least one substituent (preferably phenylene optionally having at least one substituent), biaryl optionally having at least one substituent (preferably biphenyl optionally having at least one substituent), (cyclo)alkylene optionally having at least one substituent, or formula: —Ar—X—Ar— wherein

X represents —O—, —NH—, —NPh-, —S—, —S(=O)—, —$SO_2$—, —Rf— (preferably —$CF_2$— or —$CF_2CF_2$—), or —Ar—, and Ar represents arylene optionally having at least one substituent or biaryl optionally having at least one substituent.

$R^y$ more preferably represents arylene or biaryl, each optionally having at least one substituent, further more preferably biaryl optionally having at least one substituent, and still more preferably biphenyl optionally having at least one substituent.

In the "arylene optionally having at least one substituent," "biaryl optionally having at least one substituent," and "(cyclo)alkylene optionally having at least one substituent," which are all represented by $R^y$, preferable examples of substituents include fluoro group, perfluoro organic group (preferably $C_{1-8}$perfluoro organic group, and more preferably trifluoromethyl), and pentafluorosulfanyl; more preferable examples include fluorine and perfluoro organic group (preferably $C_{1-8}$perfluoro organic group, and more preferably trifluoromethyl); and further more preferable examples include trifluoromethyl.

$R^y$ is particularly preferably the following.

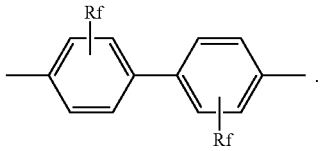

$R^y$ is particularly more preferably the following.

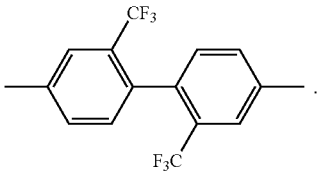

Preferable examples of fluorine-containing compound (4-3a) include the following compounds.

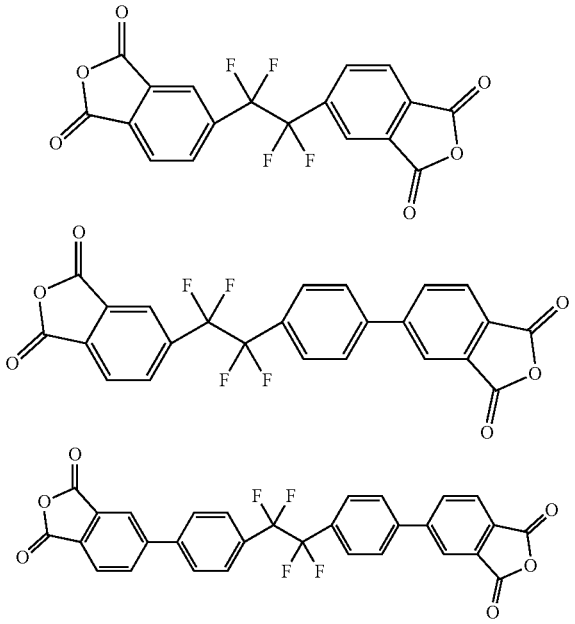

Of these, the following compound is more preferable.

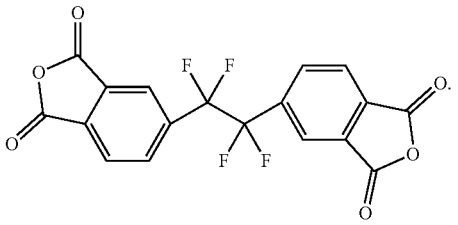

Regarding the polyimide mentioned above, fluorine-containing compound (4-3a) for use in the polyimide mentioned above may be one type, or a combination of two or more types. In other words, the units A may be the same or different at each occurrence.

Fluorine-containing compound (4-3a) can be produced by not only the production method described above but also the following method including a combination of conventional methods; specifically, fluorine-containing compound (4-3a) can be produced, for example, by oxidizing fluorine-containing compound (4-3) wherein one $R^{a1S}$ and one $R^{a2S}$ is 3,4-dimethylphenyl (which may be may be referred to hereinafter as "fluorine-containing compound (4-3i)") obtained by the production method described above with an oxidant, such as potassium permanganate (oxidation of methyl in an aromatic compound); and treating the obtained fluorine-containing compound (4-3) wherein one $R^{a1S}$ and one $R^{a2S}$ are 3,4-dicarboxyphenyl with an acid anhydride, such as acetic anhydride, to obtain fluorine-containing compound (4-3a) (intramolecular dehydration condensation of two carboxyl groups).

Examples of the diamine include diamines typically used in the production of polyimides.

Examples of the diamine include aliphatic diamines optionally having at least one fluorine atom, alicyclic diamines optionally having at least one fluorine atom, and aromatic diamines optionally having at least one fluorine atom.

The "aliphatic diamines" as used herein are diamines having no annular moiety, and are preferably aliphatic diamines having a carbon number of 1 to 6.

The "alicyclic diamines" as used herein are diamines having at least one non-aromatic ring as an annular moiety, and are preferably diamines having only at least one non-aromatic ring as an annular moiety.

The "aromatic diamines" as used herein are diamines having at least one aromatic ring as an annular moiety, and are preferably diamines having only at least one aromatic ring as an annular moiety.

The diamine preferably has a carbon number of 1 to 30, and preferably 2 to 20.

The diamine is preferably an aromatic diamine optionally having at least one trifluoromethyl.

The diamine is preferably an aromatic diamine having a carbon number of 6 to 30, and preferably 6 to 20 with optionally at least one fluorine atom.

The diamine is more preferably an aromatic diamine optionally having at least one trifluoromethyl with a carbon number of 7 to 30, and preferably 7 to 20.

Preferable examples of the diamine include the following compound.

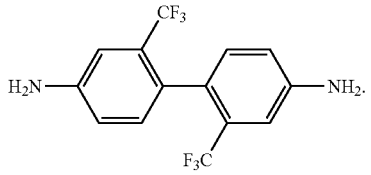

The diamine may be one type of diamine, or a combination of two or more types of diamines. In other words, the same or different structural units A may be repeated.

The polyimide mentioned above can be synthesized, for example, by a known synthesis method of polyimide, or a method according to the known method.

Specifically, polyimides can be produced by, for example, a production method comprising step P1 of reacting fluorine-containing compound (4-3a) with a diamine to obtain polyamide acid, and step P2 of heating the polyamide acid to subject the polyamide acid to a ring-closing reaction.

The molar ratio of fluorine-containing compound (4-3a) to a diamine in step P1 is typically within the range of 55:45 to 45:55, preferably 52:48 to 48:52, and more preferably 51:49 to 49:51.

Step P1 is preferably performed in the presence of a polar solvent.

Preferable examples of polar solvents include dimethylamino acetamide.

The polar solvents may be used singly or in a combination of two or more.

The reaction temperature in step P1 is typically 0 to 150° C., and preferably room temperature (25° C.) to 100° C.

The reaction time in step P1 is typically 2 to 24 hours, and preferably 2 to 12 hours.

The reaction in step P1 may be performed, for example, by stirring a solution of fluorine-containing compound (4-3a) and the diamine in a polar solvent.

After completion of the reaction in step P1, the polar solvent is preferably evaporated from the obtained product under reduced pressure.

The reaction temperature (heating temperature) in step P2 is typically within the range of 20 to 300° C., and preferably 50 to 200° C.

The reaction time in step P2 is typically within the range of 1 to 48 hours, and preferably 2 to 24 hours.

In formulae, R independently may represent alkyl or benzyl.

EXAMPLES

The following Examples describe the present invention in more detail. However, the present invention is not limited to the Examples.

The following explains the symbols used in the Examples.

br: broad
s: singlet
d: doublet
dd: double doublet
ddt: double double triplet
t: triplet
tdd: triple double doublet
m: multiplet
rt: room temperature
Calcd: calculated value
Found: measured value
phen: phenanthroline
Ph: phenyl

Example 1

Synthesis of (phen)$CuCF_2CF_2Ph$ 5,5-dimethyl-2-phenyl-1,3,2-dioxaborinane (190.1 mg, 1.0 mmol), $CuO^tBu$ (136.6 mg, 1.0 mmol), and 1,10-phenanthroline (phen: 180.1 mg, 1.0 mmol) were mixed in 10 mL of THF solvent and stirred at room temperature for 30 minutes, thereby preparing (phen)CuPh. The solution was placed in a pressure-resistant container, and TFE was pressurized to 3.5 atm, followed by heating at 40° C. for 6 hours. The unreacted TFE was degassed, and THF was added thereto to remove the insoluble solid by filtration. The filtrate was concentrated and washed with hexane, thereby giving a complex compound: (phen)$CuCF_2CF_2Ph$ as a brownish solid (387.2 mg, yield: 92%).

$^1H$ NMR (400 MHz, $CD_2Cl_2$, rt, δ/ppm): 7.35-7.47 (m, 3H), 7.60-7.73 (m, 2H), 7.80-7.91 (br, 2H), 7.91-8.11 (br, 2H), 8.41-8.64 (br, 2H), 8.93-9.21 (br, 2H). $^{19}F\{^1H\}$ NMR (376 MHz, $CD_2Cl_2$, rt, δ/ppm): major: −111.8 (br, 2F), −108.1 (br, 2F). minor: −115.9 (br, 2F), −113.6 (br, 2F).

Example 2

Examples 2-1 to 2-24 were performed using the complex compound: (phen)$CuCF_2CF_2Ph$ prepared and isolated in Example 1 by the following method A and/or method B to thereby obtain the respective target fluorine-containing compounds.

Method A (phen)$CuCF_2CF_2Ph$ (8.4 mg, 0.02 mmol) and iodoarene (0.024 mmol, 1.2 eq) were mixed in 0.5 ml of THF/THF-$d_8$ (v/v'=4/1) solvent under a nitrogen atmosphere and heated at room temperature or 60° C., thereby giving the target product. The yield was determined by $^{19}F$ NMR using α,α,α-trifluorotoluene added to the reaction solution as an internal standard.

Method B

A substrate was added to a suspension of (phen) $CuCF_2CF_2Ph$ (1.2 eq) in 10 ml of THF under a nitrogen atmosphere and heated at 60° C. for a predetermined time period. The reaction mixture was then cooled to room temperature, and 10 ml of ether was added thereto, followed by filtration to remove the insoluble matter. The filtrate was concentrated and then purified by column chromatography, thereby giving the target product.

Example 2-1

1,1,2,2-tetrafluoro-1,2-diphenylethane

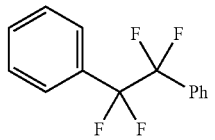

The title compound was prepared by method A as described below.

(phen)$CuCF_2CF_2Ph$ (8.4 mg, 0.02 mmol) and iodobenzene (4.9 mg, 0.024 mmol) were mixed in 0.5 ml of THF/THF-$d_8$ (v/v'=4/1) solvent under a nitrogen atmosphere and heated at 60° C. for 20 hours, thereby giving the corresponding title compound title compound at a yield of 98% (calculated from $^{19}F$ NMR).

The title compound was prepared by method B as described below.

Iodobenzene (20.4 mg, 0.10 mmol) was added to a suspension of complex (phen)$CuCF_2CF_2Ph$ (50.4 mg, 0.12 mmol) in 10 ml of THF under a nitrogen atmosphere and heated at 60° C. for 4 hours. The reaction mixture was then cooled to room temperature, and 10 ml of ether was added thereto, followed by filtration to remove the insoluble matter. The filtrate was concentrated and then purified by flash column chromatography (developing solvent hexane:ethyl acetate=99:1), thereby giving 23.4 mg (yield: 92%) of the title compound.

$^1H$ NMR (400 MHz, in $CDCl_3$, rt, δ/ppm): 7.37-7.57 (m, 10H). $^{19}F$ NMR (376 MHz, in $CDCl_3$, rt, δ/ppm): −111.8 (s, 4F). $^{13}C$ $\{^1H\}$ NMR (100.6 MHz, in $CDCl_3$, rt, δ/ppm): 116.6 (tt, $^1J_{CF}$=253.1, $^2J_{CF}$=36.5 Hz), 126.9 (tt, $J_{CF}$=3.7, 3.7 Hz), 128.0, 130.9 (t, $^2J_{CF}$=26.4). HRMS Calcd for $C_{14}H_{10}F_4$ 254.0719 found m/z 254.0718.

Example 2-2

4-(1,1,2,2-tetrafluoro-2-phenylethyl)anisole

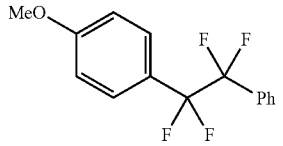

The title compound was prepared by method A as described below.

(phen)$CuCF_2CF_2Ph$ (8.4 mg, 0.02 mmol) and 4-iodoanisole (5.6 mg, 0.024 mmol) were mixed in 0.5 ml of THF/THF-$d_8$ (v/v'=4/1) solvent under a nitrogen atmosphere and heated at 60° C. for 20 hours, thereby giving the corresponding title compound at a yield of 95% (calculated from $^{19}F$ NMR).

The title compound was prepared by method B as described below.

4-iodoanisole (70.2 mg, 0.30 mmol) was added to a suspension of complex (phen)$CuCF_2CF_2Ph$ (151.2 mg, 0.36 mmol) in 10 ml of THF under a nitrogen atmosphere and heated at 60° C. for 16 hours. The reaction mixture was then cooled to room temperature, and 10 ml of ether was added thereto, followed by filtration to remove the insoluble matter. The filtrate was concentrated and then purified by flash column chromatography (developing solvent hexane:ethyl acetate=99:1), thereby giving 79.0 mg (yield: 93%) of the title compound.

$^1H$ NMR (400 MHz, in $CDCl_3$, rt, δ/ppm): 3.84 (s, 3H), 6.91 (d, J=8.7 Hz, 2H), 7.36 (d, J=8.7 Hz, 2H), 7.38-7.52 (m, 5H). $^{19}F$ NMR (376 MHz, in $CDCl_3$, rt, δ/ppm): −111.9 (s, 2F), −110.8 (s, 2F), −65.4 (s, 3F). $^{13}C\{^1H\}$ NMR (100.6 MHz, in $CDCl_3$, rt, δ/ppm): 55.3, 113.4, 116.6 (tt, $^1J_{CF}$=252.5, $^2J_{CF}$=36.7 Hz), 116.8 (tt, $^1J_{CF}$=252.5, $^2J_{CF}$=36.7 Hz), 122.9 (t, $^2J_{CF}$=25.5 Hz), 126.9 (t, $^3J_{CF}$=6.6 Hz), 128.0, 128.4 (t, $^3J_{CF}$=6.6 Hz), 130.8, 131.0 (t, $^2J_{CF}$=25.6 Hz), 161.5. HRMS Calcd for $C_{15}H_{12}F_4O$ 284.0824 found m/z 284.0826.

Example 2-3

1-trifluoromethyl-4-(1,1,2,2-tetrafluoro-2-phenylethyl)benzene

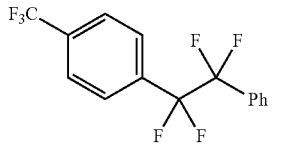

The title compound was prepared by method A as described below.

(phen)$CuCF_2CF_2Ph$ (8.4 mg, 0.02 mmol) and 4-iodobenzotrifluoride (6.5 mg, 0.024 mmol) were mixed in 0.5 ml of THF/THF-$d_8$ (v/v'=4/1) solvent under a nitrogen atmosphere and heated at 60° C. for 6 hours, thereby giving the corresponding title compound at a yield of 98% (calculated from $^{19}F$ NMR).

The title compound was prepared by method B as described below.

4-Iodobenzotrifluoride (27.2 mg, 0.10 mmol) was added to a suspension of complex (phen)$CuCF_2CF_2Ph$ (50.4 mg, 0.12 mmol) in 10 ml of THF under a nitrogen atmosphere and heated at 60° C. for 4 hours. The reaction mixture was then cooled to room temperature, and 10 ml of ether was added thereto, followed by filtration to remove the insoluble matter. The filtrate was concentrated and then purified by flash column chromatography (developing solvent hexane: ethyl acetate=99:1), thereby giving 31.2 mg (yield: 97%) of the title compound.

$^1H$ NMR (400 MHz, in $CDCl_3$, rt, δ/ppm): 7.41-7.56 (m, 5H), 7.61 (d, J=8.3 Hz, 2H), 7.70 (d, J=8.3 Hz, 2H). $^{19}F$ NMR (376 MHz, in $CDCl_3$, rt, δ/ppm): −114.3 (s, 2F), −113.8 (s, 2F), −65.4 (s, 3F). $^{13}C\{^1H\}$ NMR (100.6 MHz, in $CDCl_3$, rt, δ/ppm): 116.0 (tt, $^1J_{CF}$=253.2, $^2J_{CF}$=36.0 Hz), 116.4 (tt, $^1J_{CF}$=253.2, $^2J_{CF}$=36.0 Hz), 123.4 (q, $^1J_{CF}$=273.5 Hz, —$CF_3$), 125.1 (q, $^3J_{CF}$=3.6 Hz), 126.9 (t, $^3J_{CF}$=6.3 Hz), 127.6 (t, $^3J_{CF}$=6.3 Hz), 128.2, 130.3 (t, $^2J_{CF}$=24.4 Hz), 131.2, 133.1 (q, $^2J_{CF}$=32.1 Hz), 134.6 (t, $^2J_{CF}$=24.4 Hz). HRMS Calcd for $C_{15}H_9F_7$ 322.0592 found m/z 322.0594.

Example 2-4

2-(1,1,2,2-tetrafluoro-2-phenylethyl)mesitylene

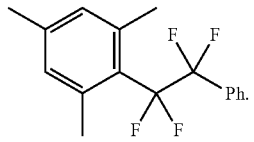

The title compound was prepared by method A as described below.

(phen)$CuCF_2CF_2Ph$ (8.4 mg, 0.02 mmol) and 2-iodine mesitylene (5.9 mg, 0.024 mmol) were mixed in 0.5 ml of THF/THF-$d_8$ (v/v'=4/1) solvent under a nitrogen atmosphere and heated at 60° C. for 140 hours, thereby giving the corresponding title compound at a yield of 83% (calculated from $^{19}F$ NMR). $^{19}F$ NMR (376 MHz, in THF/THF-$d_8$, rt, δ/ppm): −112.9 (s, 2F), −102.1 (s, 2F). MS (EI): m/z (%): 296(6) $[M]^+$, 169(100) $[(Me)_3C_6H_2CF_2]^+$, 127(14) $[PhCF_2]^+$, 77(8), 51(3).

Example 2-5

4-bromo-2-chloro-1-(1,1,2,2-tetrafluoro-2-phenylethyl)benzene

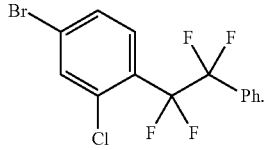

The title compound was prepared by method A as described below.

(phen)$CuCF_2CF_2Ph$ (8.4 mg, 0.02 mmol) and 4-bromo-2-chloro-1-iodobenzene (10.1 mg, 0.024 mmol) were mixed in 0.5 ml of THF/THF-$d_8$ (v/v'=4/1) solvent under a nitrogen atmosphere and heated at 60° C. for 6 hours, thereby giving the corresponding title compound at a yield of 98% (calculated from $^{19}$F NMR).

The title compound was prepared by method B as described below.

4-bromo-2-chloro-1-iodobenzene (95.2 mg, 0.30 mmol) was added to a suspension of complex (phen)$CuCF_2CF_2Ph$ (126.3 mg, 0.30 mmol) in 10 ml of THF under a nitrogen atmosphere and heated at 60° C. for 12 hours. The reaction mixture was then cooled to room temperature, and 10 ml of ether was added thereto, followed by filtration to remove the insoluble matter. The filtrate was concentrated and purified by flash column chromatography (developing solvent hexane:ethyl acetate=95:5), thereby giving 89.1 mg (yield: 81%) of the title compound.

$^1$H NMR (400 MHz, in $CDCl_3$, rt, δ/ppm): 7.38 (d, J=8.4 Hz, 1H), 7.41-7.54 (m, 6H), 7.64 (m, 1H). $^{19}$F NMR (376 MHz, in $CDCl_3$, rt, δ/ppm): −110.4 (t, $J_{FF}$=9.6 Hz, 2F), −107.6 (t, $J_{FF}$=9.6 Hz, 2F), −65.4 (s, 3F). $^{13}C\{^1H\}$ NMR (100.6 MHz, in $CDCl_3$, rt, δ/ppm): 116.2 (tt, $^1J_{CF}$=256.0, $^2J_{CF}$=38.6 Hz), 116.8 (tt, $^1J_{CF}$=253.9, $^2J_{CF}$=36.4 Hz), 125.8, 127.0 (t, $^3J_{CF}$=6.9 Hz), 127.5 (t, $^2J_{CF}$=24.4 Hz), 128.2, 129.7, 130.3 (t, $^2J_{CF}$=24.6 Hz), 131.1, 131.4 (t, $^3J_{CF}$=8.5 Hz), 134.3, 134.5 (t, $^3J_{CF}$=2.7 Hz). HRMS Calcd for $C_{14}H_8BrClF_4$ 365.9434 found m/z 365.9438.

Example 2-6

4-(1,1,2,2-tetrafluoro-2-phenylethyl)benzaldehyde

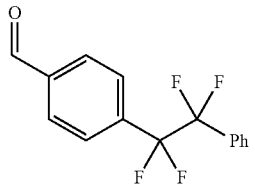

The title compound was prepared by method A as described below.

(phen)$CuCF_2CF_2Ph$ (8.4 mg, 0.02 mmol) and 4-iodobenzaldehyde (5.6 mg, 0.024 mmol) were mixed in 0.5 ml of THF/THF-$d_8$ (v/v'=4/1) solvent under a nitrogen atmosphere and heated at 60° C. for 2 hours, thereby giving the corresponding title compound at a yield of 99% (calculated from $^{19}$F NMR).

The title compound was prepared by method B as described below.

4-iodobenzaldehyde (69.6 mg, 0.30 mmol) was added to a suspension of complex (phen)$CuCF_2CF_2Ph$ (151.2 mg, 0.36 mmol) in 10 ml THF under a nitrogen atmosphere and heated at 60° C. for 4 hours. The reaction mixture was then cooled to room temperature, and 10 ml of ether was added thereto, followed by filtration to remove the insoluble matter. The filtrate was concentrated and purified by flash column chromatography (developing solvent hexane:ethyl acetate=95:5), thereby giving 84.0 mg (yield: 99%) of the title compound.

$^1$H NMR (400 MHz, in $CDCl_3$, rt, δ/ppm): 7.40-7.55 (m, 5H), 7.65 (d, J=8.3 Hz, 2H), 7.94 (d, J=8.3 Hz, 2H), 10.09 (s, 1H). $^{19}$F NMR (376 MHz, in $CDCl_3$, rt, δ/ppm): −112.2 (s, 2F), −111.5 (s, 2F). $^{13}C\{^1H\}$ NMR (100.6 MHz, in $CDCl_3$, rt, δ/ppm): 116.1 (tt, $^1J_{CF}$=253.2, $^2J_{CF}$=36.7 Hz), 116.4 (tt, $^1J_{CF}$=253.2, $^2J_{CF}$=35.5 Hz), 126.8 (t, $^3J_{CF}$=6.5 Hz), 127.8 (t, $^3J_{CF}$=6.2 Hz), 128.2, 129.2, 130.2 (t, $^2J_{CF}$=24.8 Hz), 131.1, 136.4 (t, $^2J_{CF}$=24.9 Hz), 137.9, 191.4. HRMS Calcd for $C_{15}H_{10}F_4O$ 282.0668 found m/z 282.0668.

Example 2-7

1-ethoxycarbonyl-4-(1,1,2,2-tetrafluoro-2-phenylethyl)benzene

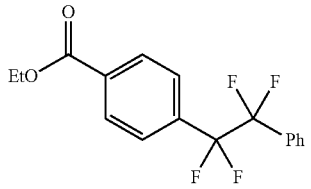

The title compound was prepared by method A as described below.

(phen)$CuCF_2CF_2Ph$ (8.4 mg, 0.02 mmol) and 4-ethoxycarbonyl-1-iodobenzene (7.8 mg, 0.024 mmol) were mixed in 0.5 ml of THF/THF-$d_8$ (v/v'=4/1) solvent under a nitrogen atmosphere and heated at 60° C. for 6 hours, thereby giving the corresponding title compound at a yield of 88% (calculated from $^{19}$F NMR).

The title compound was prepared by method B as described below.

4-ethoxycarbonyl-1-iodobenzene (32.6 mg, 0.10 mmol) was added to a suspension of complex (phen)$CuCF_2CF_2Ph$ (50.4 mg, 0.12 mmol) in 10 ml of THF under a nitrogen atmosphere and heated at 60° C. for 4 hours. The reaction mixture was then cooled to room temperature, and 10 ml of ether was added thereto, followed by filtration to remove the insoluble matter. The filtrate was concentrated and purified by flash column chromatography (developing solvent hexane:ethyl acetate=95:5), thereby giving 31.9 mg (yield: 98%) of the title compound.

$^1$H NMR (400 MHz, in $CDCl_3$, rt, δ/ppm): 1.41 (t, J=7.2 Hz, 3H), 4.41 (q, J=7.2 Hz, 2H), 7.37-7.51 (m, 5H), 7.53 (d, J=8.2 Hz, 2H), 8.08 (d, J=8.2 Hz, 2H). $^{19}$F NMR (376 MHz, in $CDCl_3$, rt, δ/ppm): −112.2 (s, 2F), −111.7 (s, 2F). $^{13}C\{^1H\}$ NMR (100.6 MHz, in $CDCl_3$, rt, δ/ppm): 14.2, 61.3, 116.3 (tt, $^1J_{CF}$=252.4, $^2J_{CF}$=36.5 Hz), 116.4 (tdd, $^1J_{CF}$=254.0, $^2J_{CF}$=38.2, 32.7 Hz), 126.8 (t, $^3J_{CF}$=6.2 Hz), 127.0 (t, $^3J_{CF}$=6.2 Hz), 128.1, 129.2, 130.4 (t, $^2J_{CF}$=25.0 Hz), 131.0, 132.9, 135.0 (t, $^2J_{CF}$=25.0 Hz), 165.6. HRMS Calcd for $C_{17}H_{14}F_4O_2$ 326.0930 found m/z 326.0929.

Example 2-8

4-(1,1,2,2-tetrafluoro-2-phenylethyl)benzonitrile

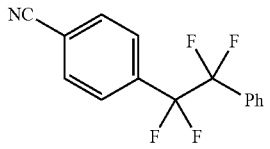

The title compound was prepared by method A as described below.

(phen)$CuCF_2CF_2Ph$ (8.4 mg, 0.02 mmol) and 4-iodobenzonitrile (5.5 mg, 0.024 mmol) were mixed in 0.5 ml of THF/THF-$d_8$ (v/v'=4/1) solvent under a nitrogen atmosphere and heated at 60° C. for 2 hours, thereby giving the corresponding title compound at a yield of 97% (calculated from $^{19}$F NMR).

The title compound was prepared by method B as described below.

4-iodobenzonitrile (68.7 mg, 0.30 mmol) was added to a suspension of complex (phen)$CuCF_2CF_2Ph$ (50.4 mg, 0.12 mmol) in 10 ml of THF under a nitrogen atmosphere and heated at 60° C. for 64 hours. The reaction mixture was then cooled to room temperature, and 10 ml of ether was added thereto, followed by filtration to remove the insoluble matter. The filtrate was concentrated and purified by flash column chromatography (developing solvent hexane:ethyl acetate=95:5), thereby giving 78.6 mg (yield: 94%) of the title compound.

$^1$H NMR (400 MHz, in $CDCl_3$, rt, δ/ppm): 7.40-7.56 (m, 5H), 7.60 (d, J=8.3 Hz, 2H), 7.72 (d, J=8.3 Hz, 2H). $^{19}$F NMR (376 MHz, in $CDCl_3$, rt, δ/ppm): −112.5 (s, 2F), −112.4 (s, 2F). $^{13}C\{^1H\}$ NMR (100.6 MHz, in $CDCl_3$, rt, δ/ppm): 115.1, 115.7 (tt, $^1J_{CF}$=254.9, $^2J_{CF}$=37.3 Hz), 116.3 (tt, $^1J_{CF}$=252.9, $^2J_{CF}$=35.3 Hz), 117.8, 126.8 (t, $^3J_{CF}$=6.6 Hz), 127.8 (t, $^3J_{CF}$=6.6 Hz), 128.3, 129.9 (t, $^2J_{CF}$=24.8 Hz), 131.3, 131.9, 135.3 (t, $^2J_{CF}$=25.6 Hz). HRMS Calcd for $C_{15}H_9F_4N$ 279.0671 found m/z 279.0670.

Example 2-9

2-(4-(1,1,2,2-tetrafluoro-2-phenylethyl))-5,5-dimethyl-1,3,2-dioxaborinane

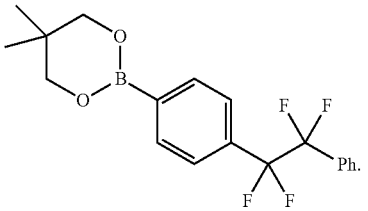

The title compound was prepared by method A as described below.

(phen)$CuCF_2CF_2Ph$ (8.4 mg, 0.02 mmol) and 2-(4-iodophenyl)-5,5-dimethyl-1,3,2-dioxaborinane (7.6 mg, 0.024 mmol) were mixed in 0.5 ml of THF/THF-$d_8$ (v/v'=4/1) solvent under a nitrogen atmosphere and heated at 60° C. for 6 hours, thereby giving the corresponding title compound at a yield of 72% (calculated from $^{19}$F NMR).

$^{19}$F NMR (376 MHz, in THF/THF-$d_8$, rt, δ/ppm): −114.6 (s, 2F), −114.4 (s, 2F). HRMS Calcd for $C_{19}H_{19}F_4O_2B$ 366.1414. found m/z 366.1412.

Example 2-10

1-(4-(1,1,2,2-tetrafluoroethyl-2-phenyl))-2-(trimethylsilyl)acetylene

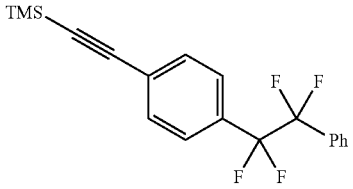

The title compound was prepared by method A as described below.

(phen)$CuCF_2CF_2Ph$ (8.4 mg, 0.02 mmol) and 1-(4-iodophenyl)-2-trimethylsilyl acetylene (7.2 mg, 0.024 mmol) were mixed in 0.5 ml of THF/THF-$d_8$ (v/v'=4/1) solvent under a nitrogen atmosphere and heated at 60° C. for 6 hours, thereby giving the corresponding title compound at a yield of 92% (calculated from $^{19}$F NMR).

$^{19}$F NMR (376 MHz, in THF/THF-$d_8$, rt, δ/ppm): −115.0 (s, 2F), −114.6 (s, 2F). HRMS Calcd for $C_{19}H_{18}F_4Si$ 350.1114 found m/z 350.1112.

Example 2-11

2-(1,1,2,2-tetrafluoro-2-phenylethyl)thiophene

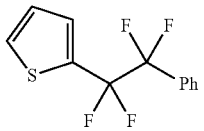

The title compound was prepared by method A as described below.

(phen)$CuCF_2CF_2Ph$ (8.4 mg, 0.02 mmol) and 2-iodothiophene (5.1 mg, 0.024 mmol) were mixed in 0.5 ml of THF/THF-$d_8$ (v/v'=4/1) solvent under a nitrogen atmosphere and heated at 60° C. for 2 hours, thereby giving the corresponding title compound at a yield of 77% (calculated from $^{19}$F NMR). MS (EI): m/z (%): 260(15) $[M]^+$, 133(100) $[C_4H_3SCF_2]^+$, 127(50) $[PhCF_2]^+$, 77(13), 51(5).

2-(1,1,2,2-tetrafluoro-2-phenylethyl)pyridine

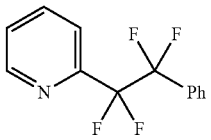

The title compound was prepared by method A as described below.

(phen)$CuCF_2CF_2Ph$ (8.4 mg, 0.02 mmol) and 2-iodopyridine (41: 4.9 mg, 0.024 mmol) were mixed in 0.5 ml of THF/THF-$d_8$ (v/v'=4/1) solvent under a nitrogen atmosphere and heated at 60° C. for 6 hours, thereby giving the corresponding title compound at a yield of 99% (calculated from $^{19}$F NMR).

The title compound was prepared by method B as described below.

2-iodopyridine (61.5 mg, 0.30 mmol) was added to a suspension of complex (phen)$CuCF_2CF_2Ph$ (151.2 mg, 0.36 mmol) in 10 ml of THF under a nitrogen atmosphere and heated at 60° C. for 4 hours. The reaction mixture was then cooled to room temperature, and 10 ml of ether was added thereto, followed by filtration to remove the insoluble matter. The filtrate was concentrated and purified by flash column chromatography (developing solvent hexane:ethyl acetate=95:5), thereby giving 74.1 mg (yield: 97%) of the title compound.

$^1$H NMR (400 MHz, in $CDCl_3$, rt, δ/ppm): 7.39-7.56 (m, 6H), 7.61 (d, J=7.8 Hz, 1H), 7.82 (t, J=7.8 Hz, 1H), 8.71 (d, J=4.2 Hz, 1H). $^{19}$F NMR (376 MHz, in $CDCl_3$, rt, δ/ppm): −114.7 (t, J=6.5 Hz, 2F), −111.1 (t, J=6.5 Hz, 2F). $^{13}C\{^1H\}$ NMR (100.6 MHz, in $CDCl_3$, rt, δ/ppm): 114.2 (tt, $^1J_{CF}$=252.8, $^2J_{CF}$=37.2 Hz), 116.5 (tt, $^1J_{CF}$=254.0 $^2J_{CF}$=34.9 Hz), 122.6 (t, $^3J_{CF}$=4.4 Hz), 125.4, 126.8 (t, $^3J_{CF}$=6.4 Hz), 128.2, 130.6 (t, $^2J_{CF}$=25.2 Hz), 131.0, 136.7, 149.4, 149.6 (t, $^2J_{CF}$=26.2 Hz). HRMS Calcd for $C_{13}H_9F_4N$ 255.0671. found m/z 255.0666.

Example 2-12

4-(1,1,2,2-tetrafluoro-2-phenylethyl)phenyl sulfurpentafluoride

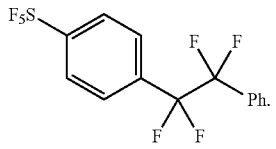

The title compound was prepared by method A as described below.

(phen)$CuCF_2CF_2Ph$ (8.4 mg, 0.02 mmol) and 4-iodophenyl sulfur pentafluoride (7.9 mg, 0.024 mmol) were mixed in 0.5 ml of THF/THF-$d_8$ (v/v'=4/1) solvent under a nitrogen atmosphere and heated at 60° C. for 2 hours, thereby giving the corresponding title compound at a yield of 90% (calculated from $^{19}$F NMR).

$^{19}$F NMR (376 MHz, in THF/THF-$d_8$, rt, δ/ppm): −114.3 (s, 2F), −113.8 (s, 2F). MS (EI): m/z (%): 380(1) $[M]^+$, 361(1), 145(4), 127 (100) $[PhCF_2]^+$, 77(7), 51(3).

Example 2-13

2-(1,1,2,2-tetrafluoro-2-phenylethyl)phenol

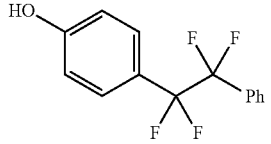

The title compound was prepared by method A as described below.

(phen)$CuCF_2CF_2Ph$ (8.4 mg, 0.02 mmol) and 4-iodophenol (5.3 mg, 0.024 mmol) were mixed in 0.5 ml of THF/THF-$d_8$ (v/v'=4/1) solvent under a nitrogen atmosphere and heated at 60° C. for 20 hours, thereby giving the corresponding title compound at a yield of 61% (calculated from $^{19}$F NMR).

$^{19}$F NMR (376 MHz, in THF/THF-$d_8$, rt, δ/ppm): −114.6 (s, 2F), −113.2 (br, 2F). MS (EI): m/z (%): 270(8) $[M]^+$, 143(100) $[HOC_6H_4CF_2]^{+,}$ 127(11) $[PhCF_2]^+$, 95(9), 75(3), 50(2).

Example 2-14

2-(1,1,2,2-tetrafluoro-2-phenylethyl)aniline

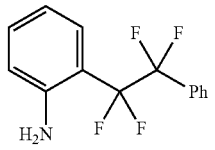

The title compound was prepared by method A as described below.

(phen)$CuCF_2CF_2Ph$ (8.4 mg, 0.02 mmol) and 2-iodoaniline (5.3 mg, 0.024 mmol) were mixed in 0.5 ml of THF/THF-$d_8$ (v/v'=4/1) solvent under a nitrogen atmosphere and heated at 60° C. for 40 hours, thereby giving the corresponding title compound at a yield of 85% (calculated from $^{19}$F NMR).

$^{19}$F NMR (376 MHz, in THF/THF-$d_8$, rt, δ/ppm): −114.5 (t, $^3J_{FF}$=5.3 Hz, 2F), −112.2 (t, $^3J_{FF}$=5.3 Hz, 2F). MS (EI): m/z (%): 269(17) $[M]^+$, 142 (100) $[H_2NC_6H_4CF_2]^+$, 127(9) $[PhCF_2]^+$, 102(11), 77(9), 51(5).

Example 2-15

4-(1,1,2,2-tetrafluoro-2-phenylethyl)phthalic anhydride

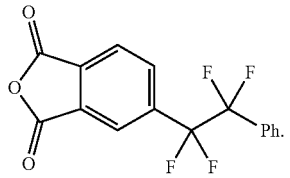

The title compound was prepared by method A as described below.

(phen)$CuCF_2CF_2Ph$ (8.4 mg, 0.02 mmol) and 4-bromophthalic anhydride (5.4 mg, 0.024 mmol) were mixed in 0.5 ml of THF/THF-$d_8$ (v/v'=4/1) solvent under a nitrogen atmosphere and heated at 60° C. for 6 hours, thereby giving the corresponding title compound at a yield of 80% (calculated from $^{19}$F NMR).

$^{19}$F NMR (376 MHz, in THF/THF-$d_8$, rt, δ/ppm): −113.9 (s, 2F), −113.4 (s, 2F). MS (EI): m/z (%): 324(2) $[M]^+$, 127(100) $[PhCF_2]^{+,}$ 107(2), 77(6), 75(6), 51(3).

Example 2-16 ethyl(Z)-4,4,5,5-tetrafluoro-5-phenylpenta-2-enoate

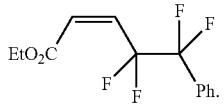

The title compound was prepared by method A as described below.

(phen)$CuCF_2CF_2Ph$ (8.4 mg, 0.02 mmol) and cis-3-iodoacrylate (5.4 mg, 0.024 mmol) were mixed in 0.5 ml of THF/THF-$d_8$ (v/v'=4/1) solvent under a nitrogen atmosphere and heated at 60° C. for 2 hours, thereby giving the corresponding title compound at a yield of 92% (calculated from $^{19}F$ NMR).

$^{19}F$ NMR (376 MHz, in THF/THF-$d_8$, rt, δ/ppm): −114.1 (s, 2F), −112.7 (d, $^3J_{HF}$=15.1 Hz, 2F). MS (EI): m/z (%): 276(1) $[M]^{+,}$ 231(3) $[PhCF_2CH{=}CHC(O)]+$, 127(100) $[PhCF_2]^+$, 77(8), 51(2).

Example 2-17

4,4,5,5-tetrafluoro-5-phenyl-1-pentene

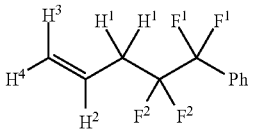

The title compound was prepared by method A as described below.

(phen)$CuCF_2CF_2Ph$ (8.4 mg, 0.02 mmol) and allyl chloride (1.8 mg, 0.024 mmol) were mixed in 0.5 ml of THF/THF-$d_8$ (v/v'=4/1) solvent under an nitrogen atmosphere and stirred at room temperature for 4 hours, thereby giving the corresponding title compound at a yield of 83% (calculated from $^{19}F$ NMR).

$^1H$ NMR (400 MHz, in $CDCl_3$, rt, δ/ppm): 2.83 (td, $^3J_{HF}$=18.0 Hz, J =7.2 Hz, 2H, $H^1$), 5.26 (dd, J=17.7, 1.2 Hz, 1H, $H^3$), 5.27 (dd, J=10.1, 1.2 Hz, 1H, $H^4$), 5.84 (ddt, J=17.7, 10.1, 7.2 Hz, 2H, $H^2$), 7.4-7.6 (m, 5H). $^{19}F$ NMR (376 MHz, in $CDCl_3$, rt, δ/ppm): −116.6 (tt, $^3J_{HF}$=18.0 Hz, $^3J_{FF}$=7.8 Hz, 2F, $F^2$), −114.5 (t, $^3J_{FF}$=7.8 Hz, 2F, $F^1$). MS (EI): m/z (%): 218(11) $[M]^+$, 203(3), 127(100) $[PhCF_2]^+$, 77(9), 51(5).

Example 2-18

1,1,2,2-tetrafluoro-1,3-diphenylpropane

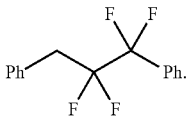

The title compound was prepared by method A as described below.

(phen)$CuCF_2CF_2Ph$ (8.4 mg, 0.02 mmol) and benzyl bromide (4.1 mg, 0.024 mmol) were mixed in 0.5 ml of THF/THF-$d_8$ (v/v'=4/1) solvent under a nitrogen atmosphere and heated at 60° C. for 2 hours, thereby giving the corresponding title compound at a yield of 32% (calculated from $^{19}F$ NMR).

$^{19}F$ NMR (376 MHz, in THF/THF-$d_8$, rt, δ/ppm): −116.6 (t, $J_{HF}$=18.5 Hz, 2F), −114.2 (s, 2F). MS (EI): m/z (%): 268 (24) $[M]^+$, 127 (100) $[PhCF_2]^+$, 91(48) $[PhCH_2]^+$, 77(10), 51(5).

Example 2-19

2,2,3,3-tetrafluoro-3-phenyl-2-butanone

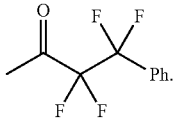

The title compound was prepared by method A as described below.

(phen)$CuCF_2CF_2Ph$ (8.4 mg, 0.02 mmol) and acetyl chloride (1.9 mg, 0.024 mmol) were mixed in 0.5 ml of THF/THF-$d_8$ (v/v'=4/1) solvent under a nitrogen atmosphere and stirred at room temperature for 1 hour, thereby giving the corresponding title compound at a yield of 78% (calculated from $^{19}F$ NMR).

$^1H$ NMR (400 MHz, in $CDCl_3$, rt, δ/ppm): 2.44 (s, 3H), 7.45-7.58 (m, 5H). $^{19}F$ NMR (376 MHz, in $CDCl_3$, rt, δ/ppm): −120.4 (t, $^3J_{FF}$=7.5 Hz, 2F), −110.6 (t, $^3J_{FF}$=7.5 Hz, 2F). HRMS Calcd for $C_{10}H_8F_4O$ 220.0511 found m/z 220.0507.

Example 2-20

1,1,2,2-tetrafluoro-1-phenyl-3-octanone

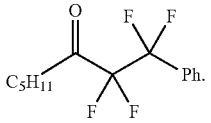

The title compound was prepared by method A as described below.

(phen)$CuCF_2CF_2Ph$ (8.4 mg, 0.02 mmol) and hexanoyl chloride (3.2 mg, 0.024 mmol) were mixed in 0.5 ml of THF/THF-$d_8$ (v/v'=4/1) solvent under a nitrogen atmosphere and stirred at room temperature for 4 hours, thereby giving the corresponding title compound at a yield of 99% (calculated from $^{19}F$ NMR).

$^{19}F$ NMR (376 MHz, in $CDCl_3$, rt, δ/ppm): −120.4 (t, $^3J_{FF}$=7.0 Hz, 2F), −110.7 (t, $^3J_{FF}$=7.0 Hz, 2F). MS (EI): m/z (%): 276(1) $[M]^+$, 127 (36) $[PhCF_2]^+$, 99 (100) $[C_5H_{11}C(O)]+$, 71 (49) $[C_5H_{11}]^+$, 55 (8).

Example 2-21

4,4,5,5-tetrafluoro-5-phenylpent-1-en-3-one

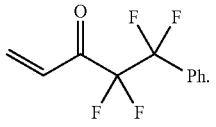

The title compound was prepared by method A as described below.

(phen)$CuCF_2CF_2Ph$ (8.4 mg, 0.02 mmol) and acryloyl chloride (2.2 mg, 0.024 mmol) were mixed in 0.5 ml of THF/THF-$d_8$ (v/v'=4/1) solvent under a nitrogen atmosphere and stirred at room temperature for 1 hour, thereby giving the corresponding title compound at a yield of 99% (calculated from $^{19}$F NMR).

$^1$H NMR (400 MHz, in $CDCl_3$, rt, δ/ppm): 6.02 (d, J=10.5 Hz, 1H), 6.62 (d, J=17.3 Hz, 1H), 6.83 (dd, J=10.5, 17.3 Hz, 1H), 7.45-7.59 (m, 5H). $^{19}$F NMR (376 MHz, in $CDCl_3$, rt, δ/ppm): −121.4 (t, $^3J_{FF}$=6.5 Hz, 2F), −110.7 (t, $^3J_{FF}$=6.5 Hz, 2F).

Example 2-22

4,4,5,5-tetrafluoro-2-methyl-5-phenylpent-1-en-3-one

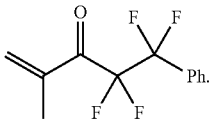

The title compound was prepared by method A as described below.

(phen)$CuCF_2CF_2Ph$ (8.4 mg, 0.02 mmol) and methacryloyl chloride (2.5 mg, 0.024 mmol) were mixed in 0.5 ml of THF/THF-$d_8$ (v/v'=4/1) solvent under a nitrogen atmosphere and stirred at room temperature for 1 hour, thereby giving the corresponding title compound at a yield of 73% (calculated from $^{19}$F NMR).

$^1$H NMR (400 MHz, in $CDCl_3$, rt, δ/ppm): 1.89 (s, 3H), 6.07 (br, 1H), 6.24 (br, 1H), 7.37-7.54 (m, 5H). $^{19}$F NMR (376 MHz, in $CDCl_3$, rt, δ/ppm): −112.2 (s, 2F), −109.9 (s, 2F).

Example 2-23

2,2,3,3-tetrafluoro-1-(4-methoxyphenyl)-3-phenyl-1-propanone

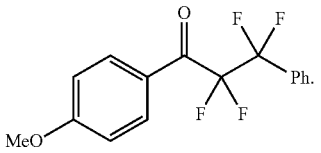

The title compound was prepared by method A as described below.

(phen)$CuCF_2CF_2Ph$ (8.4 mg, 0.02 mmol) and 4-methoxybenzoyl chloride (4.1 mg, 0.024 mmol) were mixed in 0.5 ml of THF/THF-$d_8$ (v/v'=4/1) solvent under a nitrogen atmosphere and stirred at room temperature for 1 hour, thereby giving the corresponding title compound at a yield of 94% (calculated from $^{19}$F NMR).

$^{19}$F NMR (376 MHz, in $CDCl_3$, rt, δ/ppm): −112.8 (t, $^3J_{FF}$=7.0 Hz, 2F), −109.9 (s, 2F). MS (EI) m/z (%): 312(2) $[M]^+$, 135(100) $[MeOC_6H_4C(O)]^+$, 127(7) $[PhCF_2]^+$, 107(8) $[MeOC_6H_4]^+$, 92(10), 77(19).

Example 2-24

(1) benzyl 2,2,3,3-tetrafluoro-3-phenylpropanoate

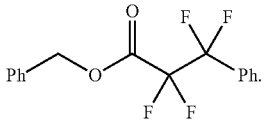

The title compound was prepared by method A as described below.

(phen)$CuCF_2CF_2Ph$ (8.4 mg, 0.02 mmol) and benzylchloroformate (4.1 mg, 0.024 mmol) were mixed in 0.5 ml of THF/THF-$d_8$ (v/v'=4/1) solvent under a nitrogen atmosphere and heated at 60° C. for 1 hour, thereby giving the corresponding title compound at a yield of 90% (calculated from $^{29}$F NMR).

The title compound was prepared by method B as described below.

Benzylchloro formate (51.2 mg, 0.30 mmol) were added to a suspension of complex (phen)$CuCF_2CF_2Ph$ (151.2 mg, 0.36 mmol) in 10 ml of THF under a nitrogen atmosphere and heated at 60° C. for 2 hours. The reaction mixture was then cooled to room temperature, and 10 ml of ether was added thereto, followed by filtration to remove the insoluble matter. The filtrate was concentrated and purified by flash column chromatography (developing solvent hexane:ethyl acetate=95:5), thereby giving 72.9 mg (yield: 78%) of the title compound.

$^1$H NMR (400 MHz, in $CDCl_3$, rt, δ/ppm): 5.34 (s, 2H), 7.34-7.47 (m, 7H), 7.49-7.58 (m, 3H). $^{19}$F NMR (376 MHz, in $CDCl_3$, rt, δ/ppm): −118.7 (t, $J_{FF}$=5.1 Hz, 2F), −111.3 (t, $J_{FF}$=5.1 Hz, 2F). $^{13}C\{^1H\}$ NMR (100.6 MHz, in $CDCl_3$, rt, δ/ppm): 69.0, 109.3 (tt, $^1J_{CF}$=262.4, $^2J_{CF}$=38.7 Hz), 115.5 (tt, $^1J_{CF}$=253.9, $^2J_{CF}$=31.4 Hz), 126.6 (t, $^3J_{CF}$=6.6 Hz), 128.4, 128.5, 128.7, 128.9, 129.2 (t, $^2J_{CF}$=24.2 Hz), 131.4, 133.7, 160.2 (t, $^2J_{CF}$=30.6 Hz). MS (EI): m/z (%): 312 (10) $[M]^+$, 158(9), 127 (29) $[PhCF_2]^+$, 91(100) $[PhCH_2]^+$, 77(9), 65(10).

(2) 2,2,3,3-tetrafluoro-3-phenylpropanoic acid

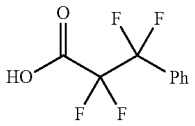

10% Pd—C(21.2 mg) was added to benzyl 2,2,3,3-tetrafluoro-3-phenylpropanoic acid ester (62.4 mg, 0.20 mmol) dissolved in 2.0 ml of ethanol, and hydrogen gas was added thereto at 2.0 atm in an autoclave, followed by a reaction at room temperature for 4 hours. After the reaction, the hydrogen gas was degassed, and the insoluble matter in the reaction mixture was removed by filtration. The obtained filtrate was concentrated under reduced pressure, thereby giving 43.2 mg (yield: 98%) of the title compound as a white solid.

$^1$H NMR (400 MHz, in $CDCl_3$, rt, δ/ppm): 7.34-7.65 (m, 5H), 7.89 (br, 1H, —COOH). $^{19}$F NMR (376 MHz, in $CDCl_3$, rt, δ/ppm): −118.9 (br, 2F, —$CF_2$COOH), −111.2 (s, 2F). $^{13}C\{^1H\}$ NMR (100.6 MHz, in $CDCl_3$, rt, δ/ppm):

109.6 (br, —$CF_2COOH$), 115.6 (tt, $^1J_{CF}$=254.5, $^2J_{CF}$=31.9 Hz), 126.7 (t, $^3J_{CF}$=6.2 Hz), 128.5, 129.0 (t, $^2J_{CF}$=24.4 Hz), 131.7, 164.1 (br, —COOH).

Example 3

Examples 3-1 to 3-11 were performed by stepwise synthesis in accordance with the following method C, thereby giving the respective target fluorine-containing compounds.

Method C

CuO$^t$Bu (2.7 mg, 0.02 mmol), 1, 10-phenanthroline (3.6 mg, 0.02 mmol), arylboronic acid ester (0.024 mmol, 1.2 eq), and α,α,α-trifluorotoluene (2.4 μL, 0.02 mmol; as an internal standard for $^{19}$F NMR) were mixed in THF/THF-$d_8$ (v/v'=4/1) solvent in an NMR tube under a nitrogen atmosphere. TFE was pressurized to 3.5 atm, and the respective reactions were allowed to proceed. After the unreacted TFE was degassed, 4-trifluoromethyl iodobenzene (6.5 mg, 0.024 mmol, 1.2 eq) was added thereto and heated at 60° C. for 4 hours. The yield of each title compound was calculated from $^{19}$F NMR.

Example 3-1

4-(1,1,2,2-tetrafluoro-2-phenylethyl)benzotrifluoride

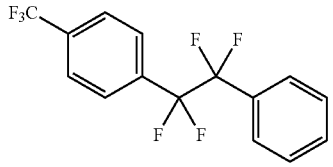

The procedure of method C was repeated using 5,5-dimethyl-2-phenyl-1,3,2-dioxaborinane (4.6 mg) as a substrate, thereby giving the title compound (a compound same as the title compound of Example 2-3) at a yield of 93%.

Example 3-2

4-(1,1,2,2-tetrafluoro-2-(1-naphthyl)ethyl)benzotrifluoride

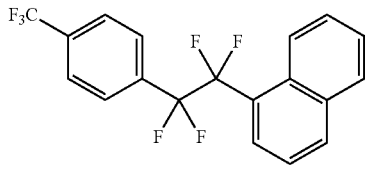

Example 3-3

The procedure of method C was repeated using 5,5-dimethyl-2-(1-naphthyl)-1,3,2-dioxaborinane (5.8 mg) as a substrate, thereby giving the title compound at a yield of 96%.

$^{19}$F NMR (376 MHz, in THF/THF-$d_8$, rt, δ/ppm): −113.1 (s, 2F), −107.0 (s, 2F), −65.7 (s, 3F). MS (EI): m/z (%): 372(13) $[M]^+$, 195(4) $[CF_3PhCF_2]^+$, 178(12), 177(100) $[C_{10}H_7CF_2]^+$, 127(10).

Example 3-4

4-(1,1,2,2-tetrafluoro-2-(4-vinylphenyl)ethyl)benzotrifluoride

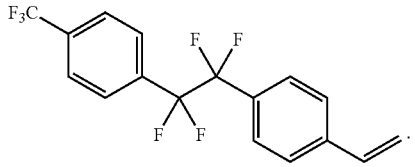

The procedure of method C was repeated using 5,5-dimethyl-2-(4-vinylphenyl)-1,3,2-dioxaborinane (5.2 mg) as a substrate, thereby giving the title compound at a yield of 89%.

$^{19}$F NMR (376 MHz, in THF/THF-$d_8$, rt, δ/ppm): −114.5 (s, 2F), −114.0 (s, 2F), −65.7 (s, 3F). MS (EI): m/z (%): 348(7) $[M]^+$, 195(4) $[CF_3PhCF_2]^+$, 154(9), 153(100) $[CH_2{=}CHC_6H_4CF_2]^+$, 133(13), 127(7), 102(4), 77(4), 51(2).

Example 3-5

4-(1,1,2,2-tetrafluoro-2-(4-methoxyphenyl)ethyl)benzotrifluoride

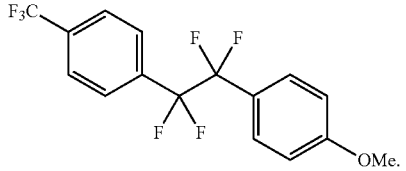

The procedure of method C was repeated using 5,5-dimethyl-2-(4-methoxy)phenyl-1,3,2-dioxaborinane (5.3 mg) as a substrate, thereby giving the title compound at a yield of 82%.

$^{19}$F NMR (376 MHz, in THF/THF-$d_8$, rt, δ/ppm): −114.6 (s, 2F), −113.0 (s, 2F), −65.7 (s, 3F). MS (EI): m/z (%): 352(4) $[M]^{+\cdot}$, 333(2), 195(3) $[CF_3PhCF_2]^+$, 158(8), 157(100) $[MeOC_6H_4CF_2]^+$, 114(12), 109(5).

Example 3-6

4-(1,1,2,2-tetrafluoro-2-(4-(tert-butyldimethylsiloxy)phenyl)ethyl)benzotrifluoride (9e)

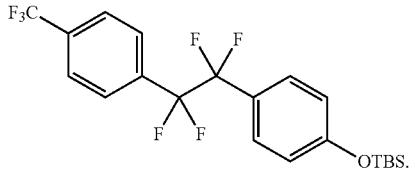

The procedure of method C was repeated using 5,5-dimethyl-2-(4-t-butyl-dimethylsiloxy)phenyl-1,3,2-dioxaborinane (7.7 mg) as a substrate, thereby giving the title compound at a yield of 92%.

$^{19}$F NMR (376 MHz, in THF/THF-$d_8$, rt, δ/ppm): −114.8 (s, 2F), −113.3 (s, 2F), −65.7 (s, 3F). MS (EI): m/z (%): 452 (16) $[M]^+$, 395(21) $[M-{}^tBu]^+$, 257(14) $[TBSOPhCF_2]^+$, 219 (100), 201(18), 77(42), 57(10).

Example 3-7

1,1,2,2-tetrafluoro-1,2-bis(4-(trifluoromethyl)phenyl)ethane

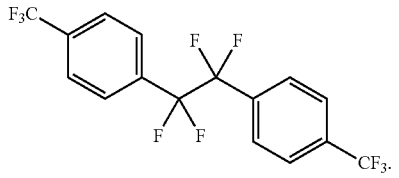

The procedure of method C was repeated using 5,5-dimethyl-2-(4-trifluoromethyl)phenyl-1,3,2-dioxaborinane (6.2 mg) as a substrate, thereby giving the title compound at a yield of 88%.

$^{19}$F NMR (376 MHz, in THF/THF-$d_8$, rt, δ/ppm): −114.0 (s, 4F), −65.8 (s, 6F). MS (EI): m/z (%): 390(1) $[M]^+$, 371(7), 195(100) $[CF_3PhCF_2]^+$, 176(3), 145(28), 126(7), 95(3), 75(3), 50(2).

Example 3-8

4-(1,1,2,2-tetrafluoro-2-(4-formylphenyl)ethyl)benzotrifluoride

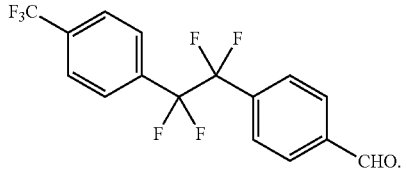

The procedure of method C was repeated using 5,5-dimethyl-2-(4-formyl)phenyl-1,3,2-dioxaborinane (5.2 mg) as a substrate, thereby giving the title compound at a yield of 82%.

$^{19}$F NMR (376 MHz, in THF/THF-$d_8$, rt, δ/ppm): −114.2 (s, 2F), −114.2 (s, 2F), −65.8 (s, 3F). MS (EI): m/z (%): 350(47) $[M]^+$, 195 (75) $[CF_3PhCF_2]^+$, 155 (100) $[CHOPhCF_2]^+$, 127 (76), 145 (24) $[CF_3Ph]^+$, 126(25), 77(14), 51(8).

Example 3-9

4-(1,1,2,2-tetrafluoro-2-(4-cyanophenyl)ethyl)benzotrifluoride

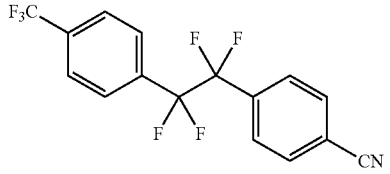

The procedure of method C was repeated using 5,5-dimethyl-2-(4-cyano)phenyl-1,3,2-dioxaborinane (5.2 mg) as a substrate, thereby giving the title compound at a yield of 47%.

$^{19}$F NMR (376 MHz, in THF/THF-$d_8$, rt, δ/ppm): −114.6 (s, 2F), −114.2 (s, 2F), −65.8 (s, 3F). MS (EI): m/z (%): 347(8) $[M]^+$, 328(6), 195(100) $[CF_3PhCF_2]^+$, 152(48) $[CNPh]^+$, 145(25) $[CF_3Ph]^+$, 127(29) $[PhCF_2]^+$, 91(100) $[PhCH_2]^+$, 77(9), 65(10).

Example 3-10

4-(1,1,2,2-tetrafluoro-2-(4-chlorophenyl)ethyl)benzotrifluoride

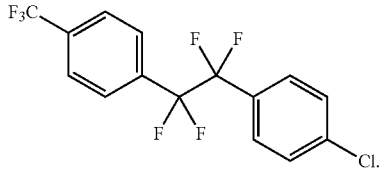

The procedure of method C was repeated using 5,5-dimethyl-2-(4-chloro)phenyl-1,3,2-dioxaborinane (5.4 mg) as a substrate, thereby giving the title compound at a yield of 94%.

$^{19}$F NMR (376 MHz, in THF/THF-$d_8$, rt, δ/ppm): −114.4 (s, 2F), −114.0 (s, 2F), −65.8 (s, 3F). MS (EI): m/z (%): 356(2) $[M]^+$, 337(3), 195(7) $[CF_3PhCF_2]^+$, 161(100) $[ClC_6H_4CF_2]^+$, 145(12), 126(12), 111(8), 75(9), 50(7).

Example 3-11

4-(1,1,2,2-tetrafluoro-2-(4-bromophenyl)ethyl)benzotrifluoride

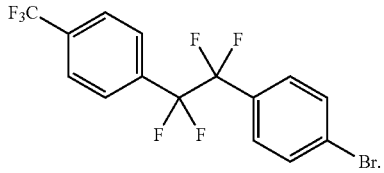

The procedure of method C was repeated using 5,5-dimethyl-2-(4-bromo)phenyl-1,3,2-dioxaborinane (6.5 mg) as a substrate, thereby giving the title compound at a yield of 100%.

$^{19}$F NMR (376 MHz, in THF/THF-$d_8$, rt, δ/ppm): −114.2 (s, 2F), −114.2 (s, 2F), −65.8 (s, 3F). MS (EI): m/z (%): 400(3) $[M]^{+,}$ 381(3), 205(100) $[BrC_6H_4CF_2]^+$, 145(20), 126 (74), 75(18), 50(8).

Example 4

In Example 4-1, the target fluorine-containing compound was obtained in one-step synthesis.

Example 4-1

Synthesis of 1,1,2,2-tetrafluoro-1,2-diphenylethane

CuO$^t$Bu (2.7 mg, 0.02 mmol), 1,10-phenanthroline (3.6 mg, 0.02 mmol), 5,5-dimethyl-2-phenyl-1,3,2-dioxaborinane (3.8 mg, 0.02 mmol), iodobenzene (4.9 mg, 0.024 mmol, 1.2 eq), and α,α,α-trifluorotoluene (2.4 μL, 0.02 mmol; as an internal standard for $^{19}$F NMR) were mixed in 0.5 ml of THF/THF-$d_8$ (v/v'=4/1) solvent in an NMR tube under a nitrogen atmosphere. TFE was pressurized to 3.5 atm, and the mixture was heated at 60° C. for 20 hours. $^{19}$F NMR confirmed the generation of the target product 1,1,2,2-tetrafluoro-1,2-diphenylethane at a yield of 83%.

Example 5

Synthesis of Polyimide

Synthesis Example 1

Synthesis of 1,2-bis(3,4-dimethylphenyl)tetrafluoroethane (Compound 1)

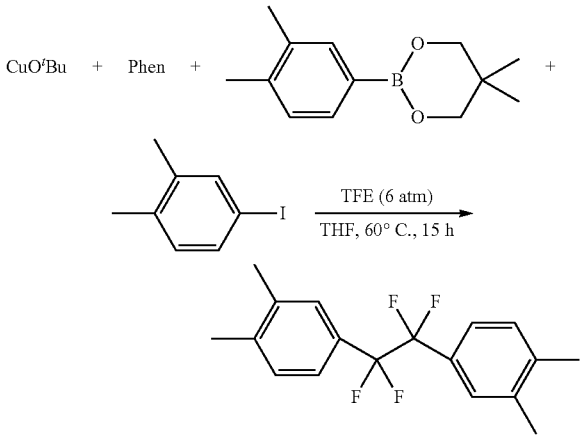

1
12%

A solution of 5,5-dimethyl-2-(3,4-dimethylphenyl)-1,3,2-dioxaborinane (819 mg, 3.5 mmol), CuO'Bu (483 mg, 3.5 mmol), and 1,10-phenanthroline (Phen: 630 mg, 3.5 mmol) in THF (25 mL) was prepared in a 50-mL pressure-resistant glass container under a nitrogen atmosphere. TFE was added to the solution using a gas feeding line (6 atm). The obtained solution was then heated at 60° C. for 15 hours with stirring. The unreacted TFE was degassed, and the produced liquid was subjected to Celite filtration. The Celite was washed with THF, and the liquid was combined with the THF solution obtained in advance, followed by concentration under reduced pressure. The obtained concentrate was purified by column chromatography ($SiO_2$, n-hexane), thereby giving 130.0 mg of the target product (compound 1) (yield 12%).

Compound 1: $^1$H NMR (396 MHz, in $CDCl_3$, δ/ppm): 2.31 (s, 6H), 2.32 (s, 6H), 7.19 (d, J=7.7 Hz, 2H), 7.22 (d, J=7.7 Hz, 2H), 7.31 (s, 2H). $^{19}$F NMR (373 MHz, in $CDCl_3$, δ/ppm): −110.52 (s). MS (EI) m/z 310 (M+). HRMS calcd for $C_{18}H_{18}F_4$ 310.1345. found 310.1344

Synthesis Example 2

Synthesis of 1,2-bis(3,4-dicarboxyphenyl)tetrafluoroethane (Compound 2)

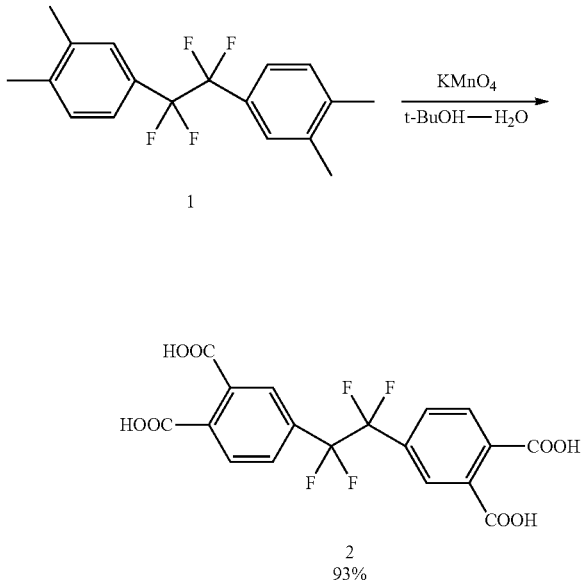

1

2
93%

Compound 1 (310 mg, 1.0 mmol) and a solution of potassium permanganate (3.8 g, 24.0 mmol) in t-Butanol (5 mL)-water (20 mL) was heated at 100° C. for 2 days with stirring. After cooling, the reaction mixture was subjected to Celite filtration using saturated sodium bicarbonate water, and the obtained aqueous solution was acidified with concentrated hydrochloric acid. The precipitated compound 2 (400 mg, yield 93%) was filtered.

Compound 2 (Na salt): $^1$H NMR (400 MHz, in $D_2O$, δ/ppm): 7.23 (d, J=8.0 Hz, 2H), 7.29 (d, J=8.0 Hz, 2H), 7.49 (s, 2H). $^{19}$F NMR (376 MHz, in $D_2O$, δ/ppm): −112.19 (s).

MS (FAB−) m/z 429 (M−1). HRMS calcd for $C_{18}H_9F_4O_8$ (M−1) 429.0234. found 429.0231

Synthesis Example 3

Synthesis of 1,2-bis(3,4-dicarboxyphenyl)tetrafluoroethane anhydride (Acid Anhydride Derivative 3)

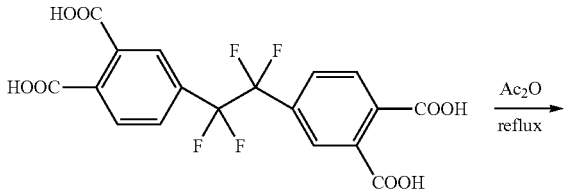

2

-continued

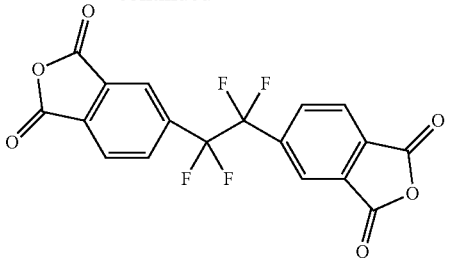

3
95%

A suspension of compound 2 (400 mg, 0.93 mmol) in acetic anhydride was stirred under reflux for 15 hours. After cooling, the reaction mixture was concentrated under reduced pressure, thereby giving acid anhydride derivative 3 (347 mg, yield 95%).

Acid anhydride derivative 3: $^{1}$H NMR (400 MHz, in $CDCl_3$, δ/ppm): 8.23 (d, J=8.0 Hz, 2H), 8.26 (d, J=8.0 Hz, 2H), 8.27 (s, 2H).

$^{19}$F NMR (376 MHz, in $CDCl_3$, δ/ppm): −109.77 (s).

MS (FAB+) m/z 395 (M+1). HRMS calcd for $C_{1\text{-}8}H_7F_4O_6$ (M+1) 395.0179. found 395.0181

Synthesis Example 4

Synthesis of Polyimide (Compound 5)

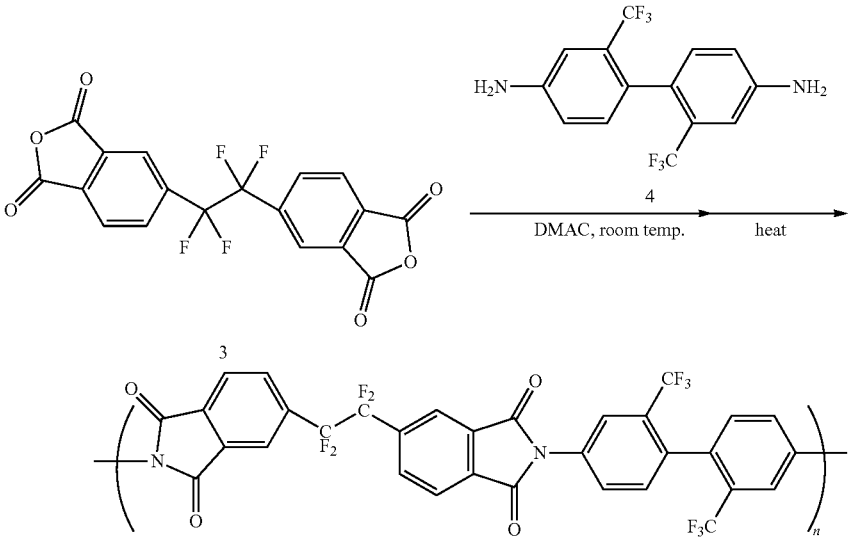

A solution of acid anhydride derivative 3 (40 mg, 0.1 mmol) and diamine derivative 4 (32 mg, 0.1 mmol) in dimethylamino acetamide (DMAC) (1 mL) was stirred in a 5 mL-eggplant flask at room temperature for 48 hours. The solvent was evaporated from the solution under reduced pressure. The remaining amide carboxylic acid derivative was heated at 190° C. for 15 hours. A film of polyimide was formed on the glass wall of the flask. The measurement of the flask weight before and after the reaction indicated the quantitative formation of a polyimide (compound 5) (79 mg).

Compound 5: IR (KBr, $cm^{-1}$): 1770, 1718, 1700, 1685, 1628, 1560, 1542, 1509, 1489, 1419, 1335, 1259, 1224, 1170, 1119, 1053.

The invention claimed is:

1. A fluorine-containing compound represented by formula (4-1):

$$(R^{a1S}—)_{ma1}R^{a1L}—CF_2—CF_2—R^{a2L}(—R^{a2S})_{ma2} \quad (4\text{-}1)$$

wherein the moiety represented by formula:$(R^{a1S}—)_{ma1}R^{a1L}$ indicates $R^{a1L}$ substituted with ma1 $R^{a1S}$;

the moiety represented by formula: $R^{a2L}(—R^{a2S})_{ma2}$ indicates $R^{a2L}$ substituted with ma2 $R^{a2S}$;

$R^{a1S}$ and $R^{a2S}$ are the same or different, and each represents independently a moiety selected from the group consisting of (1) aldehyde,

[(2) alkenyl optionally substituted with at least one halogen atom, (3)] *(2)* alkynyl optionally substituted with at least one substituent selected from the group consisting of halogen and trimethylsilyl, *and*

[(4) epoxy, (5) (meta)acryloyl optionally substituted with at least one halogen atom, and (6)] *(3)* alkyl and alkoxy each substituted with at least one substituent selected from the group consisting of:

(a) cyano group, (b) aldehyde, (c) alkynyl optionally substituted with at least one halogen atom, (d) [vinyl] *alkenyl* optionally substituted with at least one halogen atom, (e) epoxy, and (f) [(meta)acryloyl] *(meth)acryloyl* optionally substituted with at least one halogen atom, ma1 and ma2 are independently 0 or 1, and the sum of ma1 and ma2 is 1 or 2 ;

$R^{a1L}$ and $R^{a2L}$ are the same or different, and each represents a phenyl group optionally having, in addition to ma1 $R^{a1S}$ or ma2 $R^{a2S}$, at least one substituent selected from the group consisting of fluoro group, perfluoro organic group, and pentafluorosulfanyl.

2. A fluorine-containing compound represented by formula (4-3):

$$(R^{a1S}—)_{ma1}R^{a1L}—CF_2—CF_2R^{a2L}(—R^{a2S})_{ma2} \quad (4\text{-}3),$$

wherein the moiety represented by $(R^{a1S}—)_{ma1}R^{a1L}$ indicates $R^{a1L}$ substituted with ma1 $R^{a1S}$; [p1]

the moiety represented by $R^{a2L}(—R^{a2S})_{ma2}$ indicates $R^{a2L}$ substituted with ma2 $R^{a2S}$;

$R^{a1S}$ represents [1,3-dioxo-1,3-dihydroisobenzofuran 5-yl] *1,3-dioxo-1,3-dihydroisobenzofuran-5-yl;*

$R^{a2S}$ represents (1) [1,3-dioxo-1,3-dihydroisobenzofuran 5-yl] *1,3-dioxo-1,3-dihydroisobenzofuran-5-yl*, (2) amino, (3) carboxy at para-position, or (4) halogenocarbonyl;

ma1 is 1;

ma2 is 0 or 1; and $R^{a1L}$ and $R^{a2L}$ are the same or different, and each represents (a) a phenyl group or a biphenyl group, or (b) a bond, with the proviso that when $R^{a2S}$ is (2) amino, (3) carboxy at para-position, or (4) halogenocarbonyl, $R^{a2L}$ is (a) a phenyl group or a biphenyl group.

3. The fluorine-containing compound according to claim 1, wherein $R^{a1S}$ and $R^{a2S}$ are the same or different, and each represents independently a moiety selected from the group consisting of (1) [cyano, (2)] aldehyde, [(3) alkenyl, (4)] (*2*) alkynyl optionally substituted with trimethylsilyl, [(5) epoxy, (6) (meta)acryloyl optionally substituted with at least one halogen atom,] and [(7)] (*3*) alkoxy substituted with epoxy.

4. The fluorine-containing compound according to claim 1, which is selected from the following compounds:

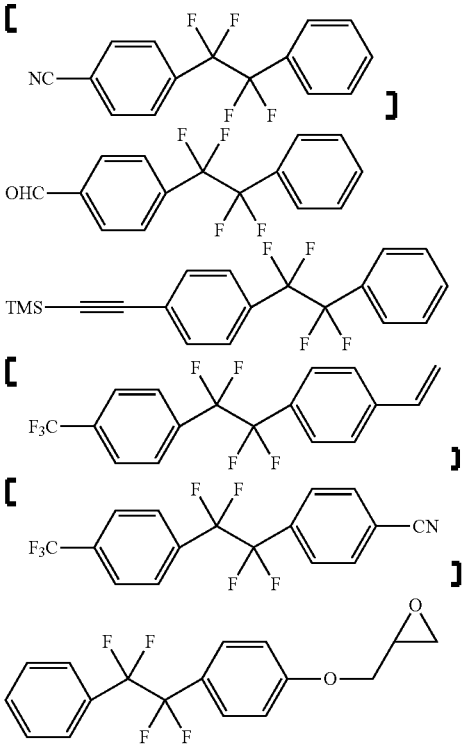

-continued

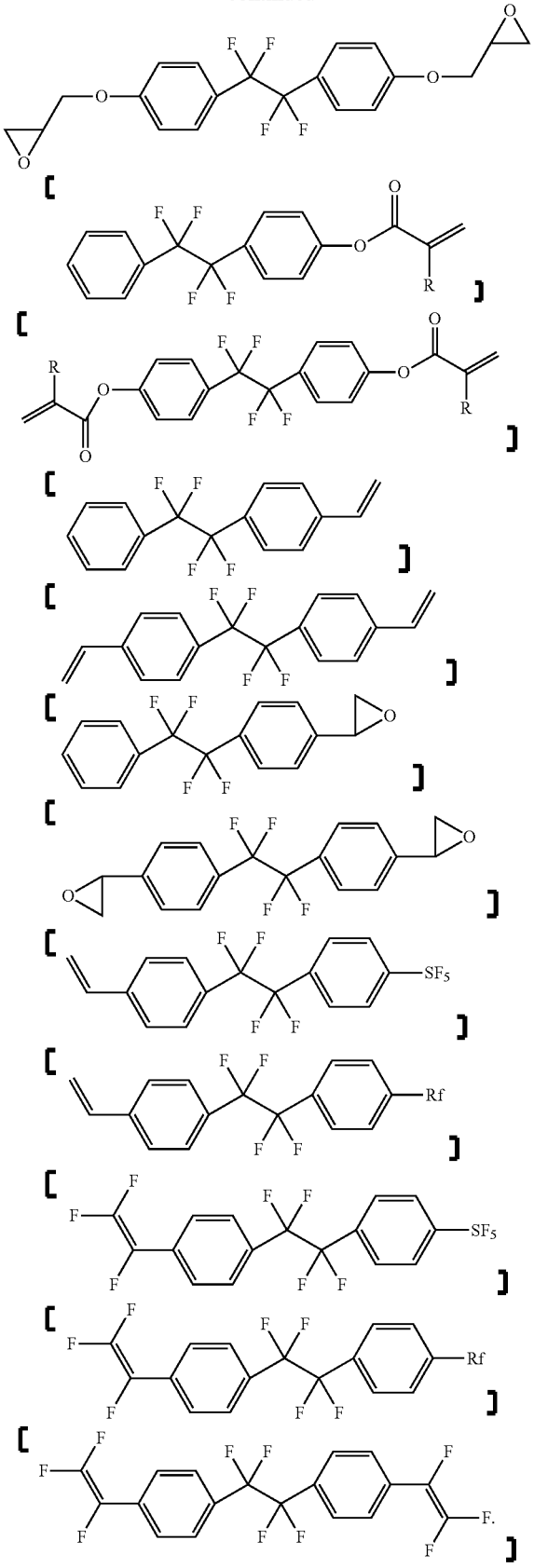

*wherein TMS represents a trimethylsilyl group.*

5. The fluorine-containing compound according to claim 2, which is selected from the following compounds:

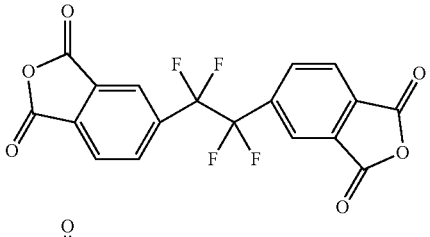

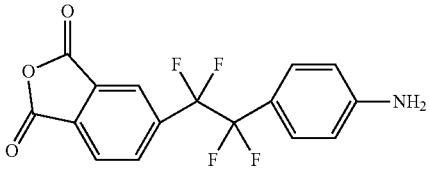

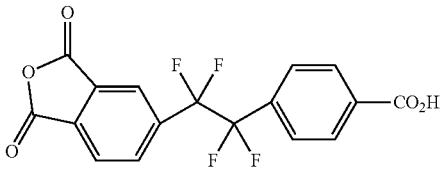

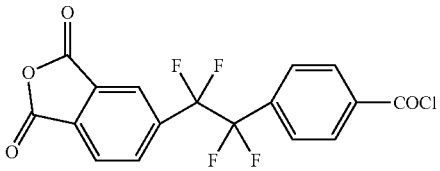

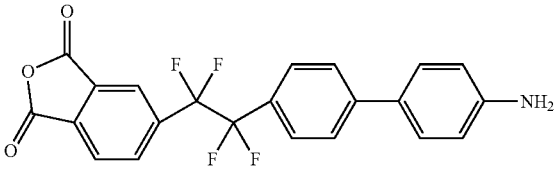

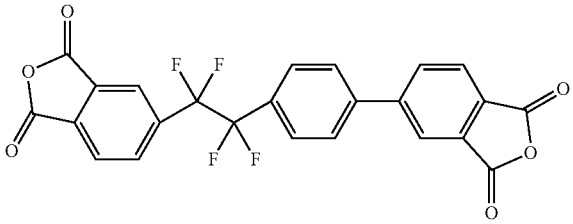

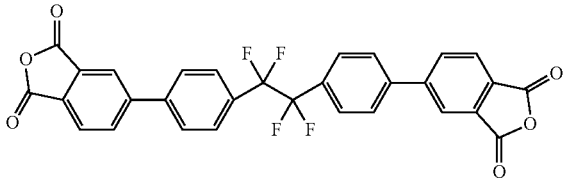

-continued

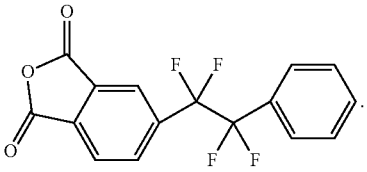

6. A method for producing the fluorine-containing compound according to claim 1, the method comprising reacting a fluorine-containing complex compound comprising:

a fluorine-containing organic metal compound represented by formula (1a):

$$R^1—CF_2—CF_2—M^1 \quad (1a)$$

wherein $M^1$ is a metal selected from the group consisting of copper, zinc, nickel, iron, cobalt, and tin; and $R^1$ represents $(R^{a1S}—)_{ma1}R^{a1L}$ as defined above, and at least one ligand selected from the group consisting of pyridine ring-containing compounds and phosphines[-fluorine-containing complex compound], with a halogen compound represented by formula (5):

$$X—R^2 \quad (5)$$

wherein $R^2$ represents $R^{a2L}(—R^{a2S})_{ma2}$ as defined above; and X represents a halogen atom.

7. A method for producing the fluorine-containing compound according to claim 2, the method comprising reacting a fluorine-containing complex compound comprising:

a fluorine-containing organic metal compound represented by formula (1a):

$$R^1—CF_2—CF_2—M^1 \quad (1a)$$

wherein $M^1$ is a metal selected from the group consisting of copper, zinc, nickel, iron, cobalt, and tin; and $R^1$ represents $(R^{a1S}—)_{ma1}R^{a1L}$ as defined above, and at least one ligand selected from the group consisting of pyridine ring-containing compounds and phosphines[-fluorine-containing complex compound], with a halogen compound represented by formula (5):

$$X—R^2 \quad (5)$$

wherein $R^2$ represents $R^{a2L}(—R^{a2S})_{ma2}$ as defined above; and X represents a halogen atom.

* * * * *